United States Patent
Boyer et al.

(10) Patent No.: US 12,426,547 B2
(45) Date of Patent: Sep. 30, 2025

(54) DEVICE AND METHOD FOR POLLEN COLLECTION

(71) Applicant: Monsanto Technology LLC, St. Louis, MO (US)

(72) Inventors: Zachary Boyer, Fenton, MO (US); Plinio Tadeu Cristofoletti, Jr., Uberlandia (BR); Justin Scott Kayser, Wentzville, MO (US); Jeffrey Steven Morris, Saint Charles, MO (US); Payman Rassoolkhani, Maryland Heights, MO (US); Felipe Camargo Rosa, Uberlandia (BR)

(73) Assignee: Monsanto Technology LLC, Saint Louis, MO (US)

( * ) Notice: Subject to any disclaimer, the term of this patent is extended or adjusted under 35 U.S.C. 154(b) by 1186 days.

(21) Appl. No.: 17/306,399

(22) Filed: May 3, 2021

(65) Prior Publication Data
US 2021/0337736 A1    Nov. 4, 2021

Related U.S. Application Data

(60) Provisional application No. 63/019,897, filed on May 4, 2020.

(51) Int. Cl.
| | | |
|---|---|---|
| *A01D 93/00* | (2009.01) | |
| *A01D 46/00* | (2006.01) | |
| *A01H 1/02* | (2006.01) | |

(52) U.S. Cl.
CPC ............ *A01D 93/00* (2013.01); *A01D 46/00* (2013.01); *A01H 1/027* (2021.01)

(58) Field of Classification Search
CPC ........ A01D 45/30; A01D 46/00; A01D 93/00; A01H 1/00–1/129; A01H 1/027;
(Continued)

(56) References Cited

U.S. PATENT DOCUMENTS

| | | | | |
|---|---|---|---|---|
| 3,670,479 A | * | 6/1972 | Tomlinson | B04C 3/00 55/416 |
| 4,038,056 A | * | 7/1977 | Diachuk | F24C 15/20 454/56 |

(Continued)

FOREIGN PATENT DOCUMENTS

| | | | |
|---|---|---|---|
| CN | 106605499 A | * | 5/2017 |
| CN | 107787832 A | * | 3/2018 |

(Continued)

*Primary Examiner* — Joseph M Rocca
*Assistant Examiner* — Madeline I Runco
(74) *Attorney, Agent, or Firm* — Harness, Dickey & Pierce, P.L.C.

(57) ABSTRACT

A pollen collection device for collecting pollen from crop plants grown in rows includes a housing assembly configured to be mounted on a base for being transported through a row of crop plants. The housing assembly receives at least a portion of the plants as the housing assembly is transported through the row of crop plants. An agitation assembly is attached to the housing assembly for agitating the plants as the housing assembly is transported through the row of crop plants to displace pollen from the plants. A pollen collection assembly is attached to the housing assembly for collecting the pollen displaced from the plants as the housing assembly is transported through the row of crop plants.

19 Claims, 21 Drawing Sheets

(58) Field of Classification Search
CPC ...... B04C 3/00–3/06; B07B 7/00–7/12; B01D 45/00–45/18
See application file for complete search history.

(56) References Cited

U.S. PATENT DOCUMENTS

| | | | |
|---|---|---|---|
| 4,087,937 A | 5/1978 | Meader | |
| 4,922,651 A * | 5/1990 | Atkinson | A01H 1/027 47/1.41 |
| 5,178,656 A * | 1/1993 | Schott | B04C 3/06 55/463 |
| 5,689,914 A * | 11/1997 | Greaves | A01N 3/00 47/1.41 |
| 6,141,904 A * | 11/2000 | Greaves | A01H 1/022 47/1.41 |
| 6,312,594 B1 * | 11/2001 | Conrad | B04C 3/00 55/459.3 |
| 7,156,889 B1 * | 1/2007 | Swanson | B01D 46/62 55/467 |
| 8,272,162 B2 * | 9/2012 | LaFargue | A23B 7/05 435/410 |
| 8,356,464 B2 * | 1/2013 | Lafargue | A01D 46/005 56/13.1 |
| 8,375,690 B2 * | 2/2013 | LaFargue | A01D 45/00 56/13.1 |
| 2006/0053686 A1 * | 3/2006 | Halwas | A01H 1/027 47/1.41 |
| 2009/0235823 A1 * | 9/2009 | Tan | B01D 45/12 55/447 |
| 2011/0023433 A1 * | 2/2011 | Lafargue | A01D 45/00 56/13.3 |
| 2014/0250625 A1 * | 9/2014 | Huang | B01D 45/12 95/271 |
| 2021/0045306 A1 * | 2/2021 | Baldet | A01B 59/064 |

FOREIGN PATENT DOCUMENTS

| | | | |
|---|---|---|---|
| CN | 209787906 U | * | 12/2019 |
| DE | 550728 C | | 5/1932 |
| FR | 2979798 A1 | | 3/2013 |
| JP | S61260819 A | * | 11/1986 |
| KR | 19990068833 A | * | 9/1999 |
| SU | 1194315 A1 | | 11/1985 |
| SU | 1606037 A1 | * | 11/1990 |

* cited by examiner

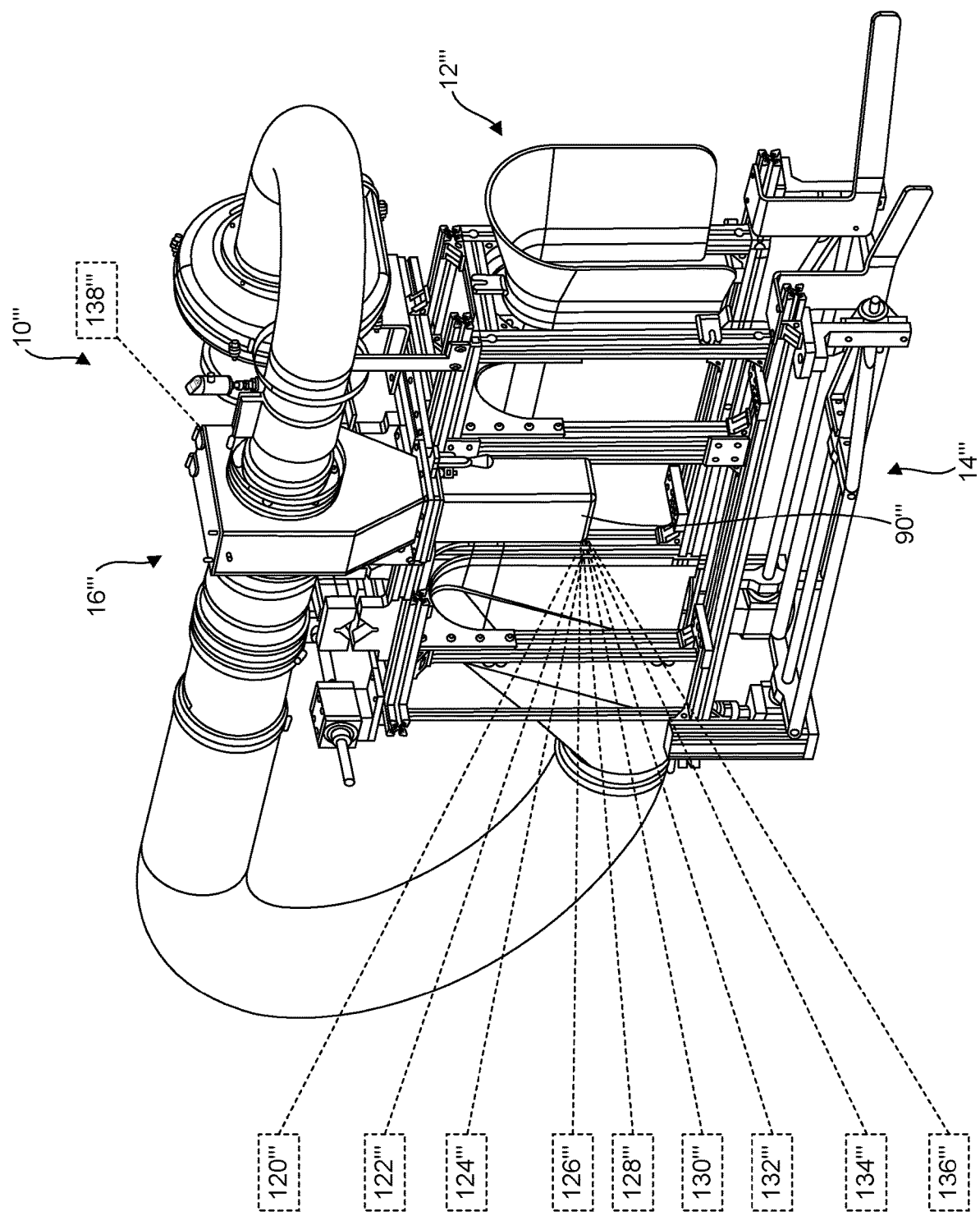

DEVICE AND METHOD FOR POLLEN COLLECTION

CROSS-REFERENCE TO RELATED APPLICATION

This application claims priority to U.S. Provisional Patent Application No. 63/019,897, entitled DEVICE AND METHOD FOR POLLEN COLLECTION and filed May 4, 2020, which is hereby incorporated by reference in its entirety.

FIELD

The present disclosure relates to a device and method for collecting pollen from crop plants, and more specifically to a device mountable on a tractor for traveling along rows of crop plants to collect pollen from the plants and related methods.

BACKGROUND

Modern agriculture often requires the retrieval or harvesting of pollen from plants for use in subsequent processes such as seed pollination processes. Particularly for corn plants, the pollen collection process typically involves placing bags over the male parts and agitating the male parts to liberate pollen into the bag. The process is labor intensive and not well suited for large-scale field collection.

Currently, pollen quantities are measured by visual inspection in production fields by shaking the corn plants (i.e., the tassels) and estimating tassel size and pollen volume. This process does not allow for precise volume estimation as it is based purely on human visual inspection. Additional assessments such as granular quantity estimation is also not achievable with this process.

SUMMARY

In one aspect, a pollen collection device for collecting pollen from crop plants grown in rows generally comprises a housing assembly configured to be mounted on a base for being transported through a row of crop plants. The housing assembly receives at least a portion of the plants as the housing assembly is transported through the row of crop plants. An agitation assembly is attached to the housing assembly for agitating the plants as the housing assembly is transported through the row of crop plants to displace pollen from the plants. A pollen collection assembly is attached to the housing assembly for collecting the pollen displaced from the plants as the housing assembly is transported through the row of crop plants.

In another aspect, a method of collecting pollen from crop plants grown in rows generally comprises transporting a pollen collection device along a row of crop plants. Displacing pollen from the row of crop plants by contacting an agitator of the pollen collection device with the crop plants as the pollen collection device is transported along the row of crop plants. Collecting the displaced pollen from the row of crop plants in the pollen collection device as the pollen collection device is transported along the row of crop plants.

In yet another aspect, a pollen collection device for collecting pollen from crop plants grown in rows generally comprises a housing assembly configured to be mounted on a base for being transported through a row of crop plants. The housing assembly receives at least a portion of the plants as the housing assembly is transported through the row of crop plants. A pollen collection assembly is attached to the housing assembly for collecting the pollen from the plants as the housing assembly is transported through the row of crop plants. A measurement device measures a characteristic of the collected pollen.

BRIEF DESCRIPTION THE DRAWINGS

Figure 11:
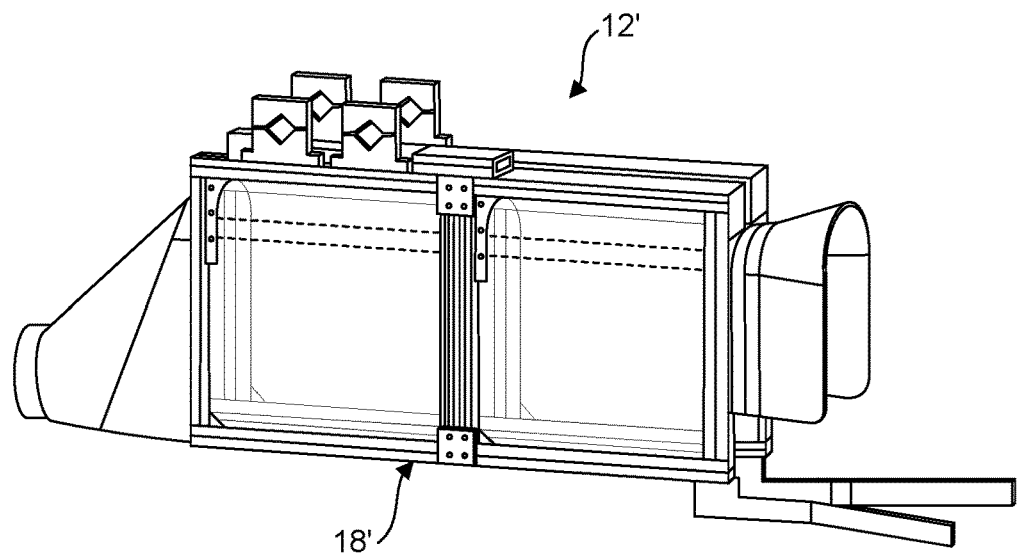
Figure 12:
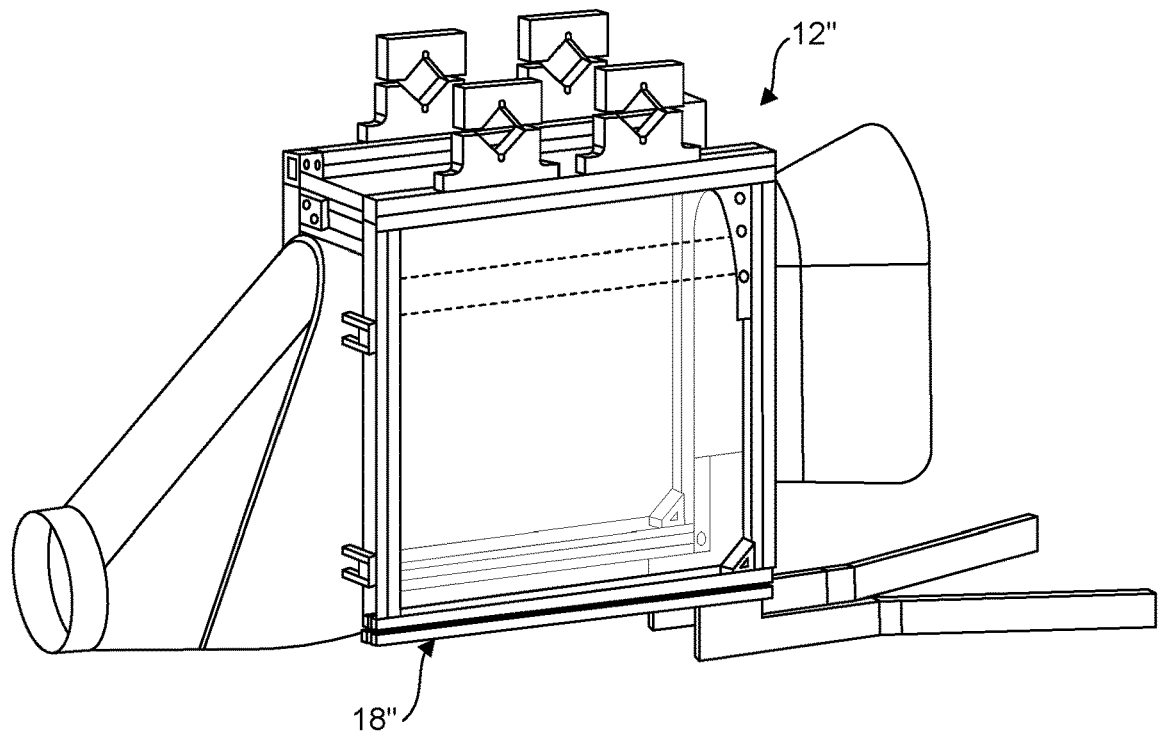
Figure 13:
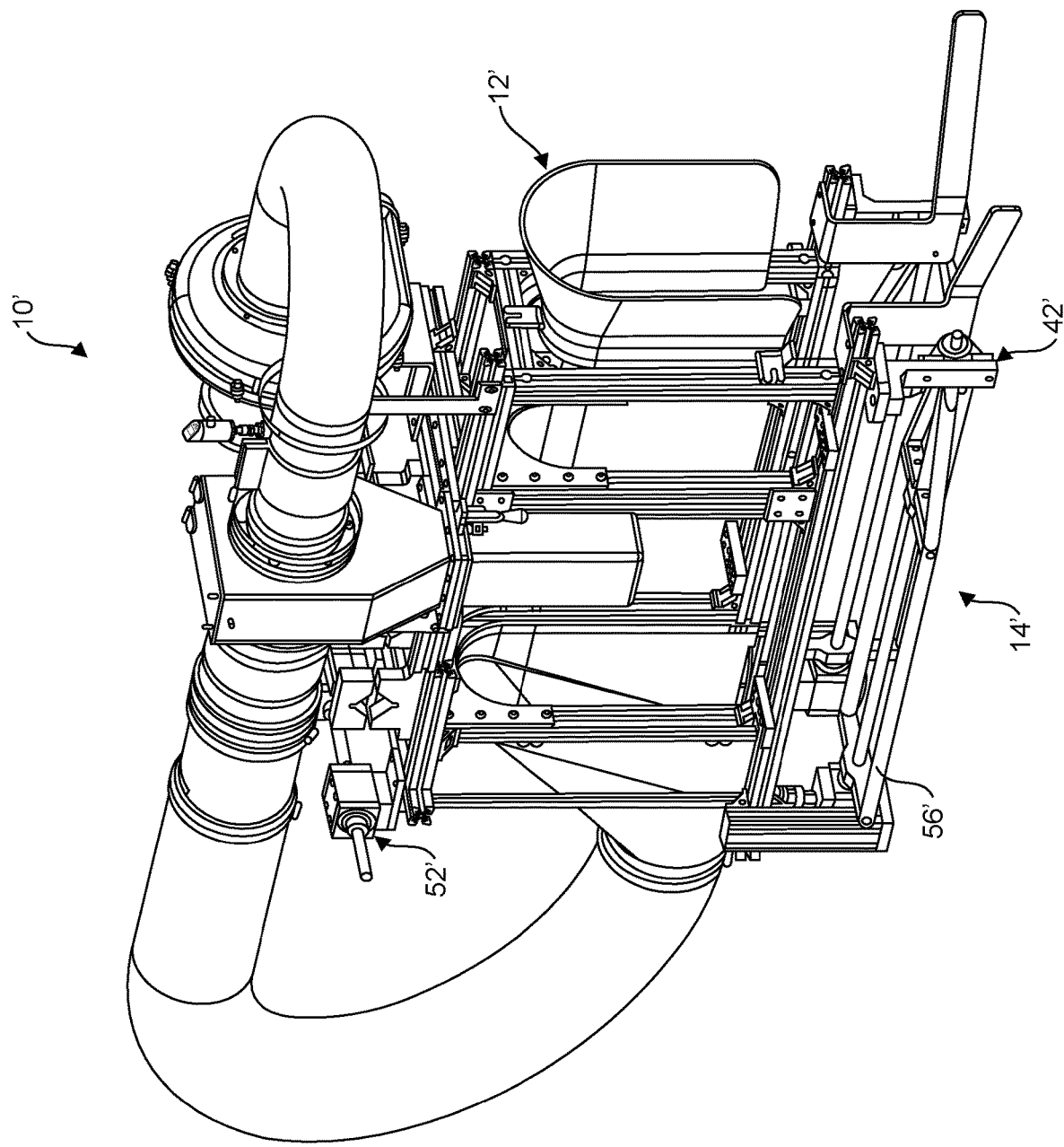
Figure 14:
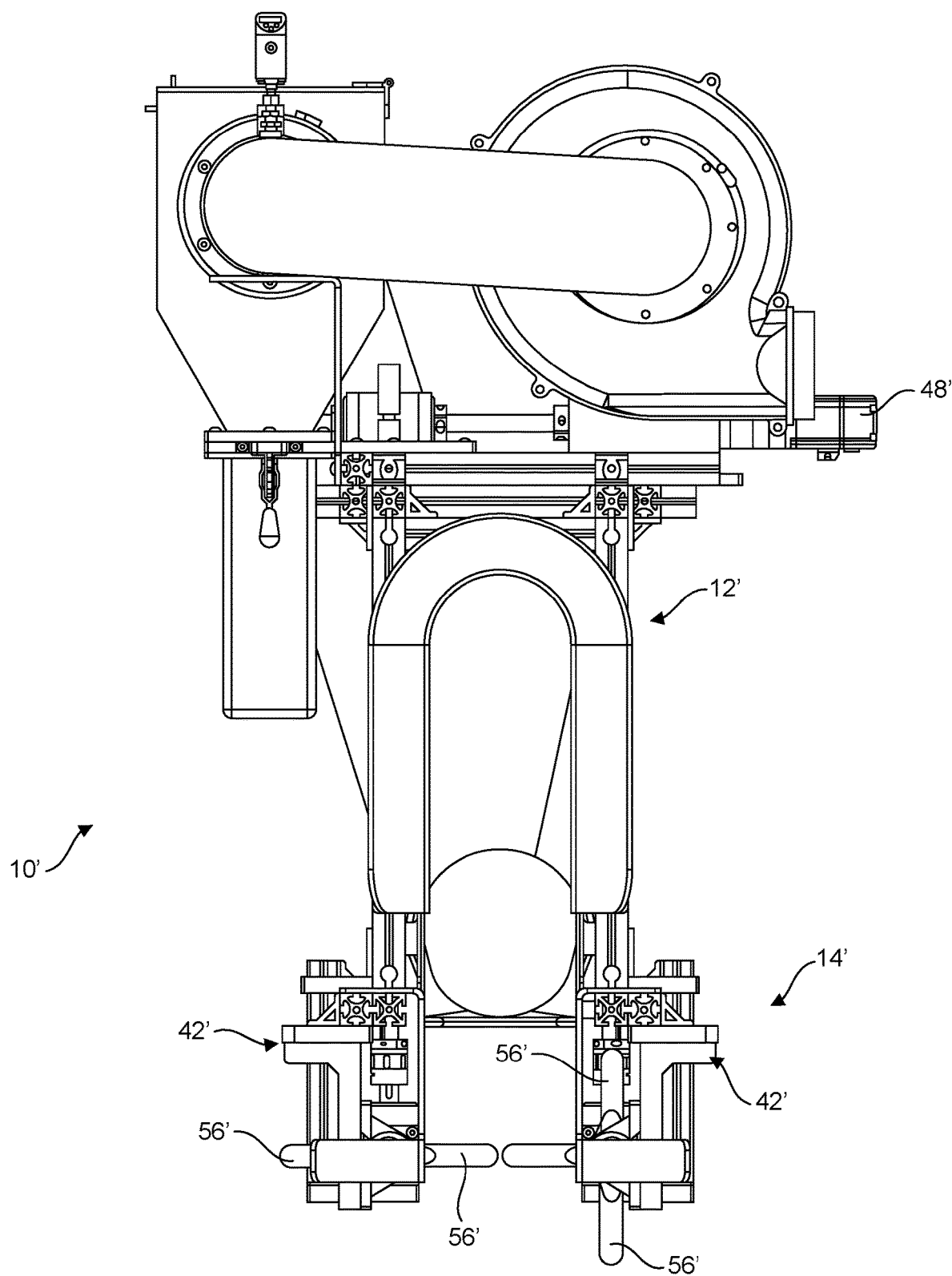

FIGS. 10A-F are perspectives of alternative vane insert configurations;

FIG. 11 is a perspective of another embodiment of a housing assembly for the pollen collection device;

FIG. 12 is a perspective of another embodiment of a housing assembly for the pollen collection device;

FIG. 13 is a perspective of a pollen collection device including another embodiment of an agitation assembly;

FIG. 14 is an end view of the pollen collection device of FIG. 13; and

FIG. 15 is a perspective of another embodiment of a pollen collection device.

Corresponding reference characters indicate corresponding parts throughout the drawings.

DETAILED DESCRIPTION

Figure 1A:
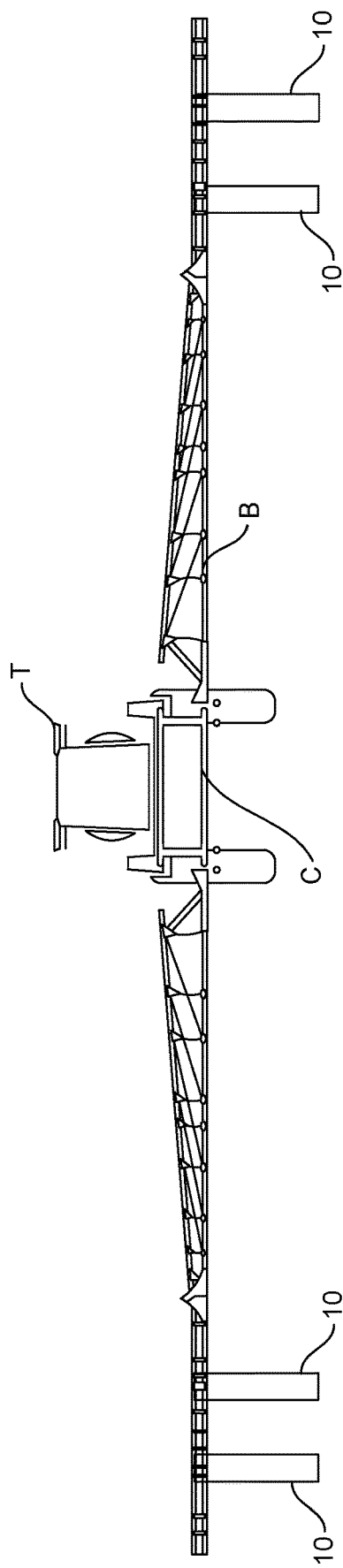
FIG. 1A is a schematic illustration of a tractor equipped with a plurality of pollen collection devices.
Figure 1B:
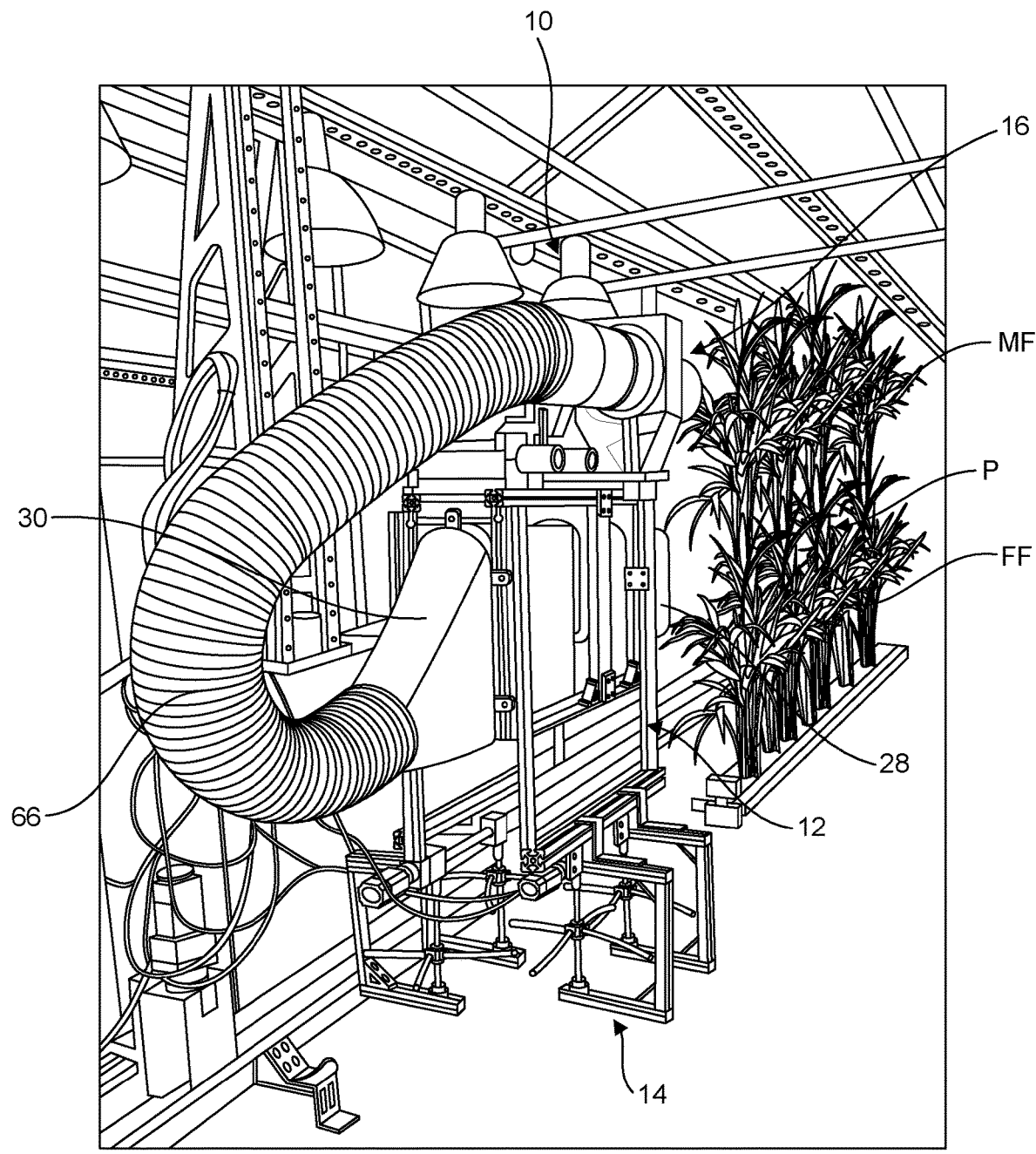
FIG. 1B is an illustration of a pollen collection device arranged for movement through a row of crop plants.

Referring to FIGS. 1A and 1B, a tractor T may be configured to carry one or more pollen collection devices, generally indicated at 10, for collecting pollen from crops plants in a field. In one embodiment, the pollen collection device 10 is configured to collect pollen from corn plants P. However, it is understood that in other embodiments a pollen collection device can be configured to collect pollen from other crop plants such as, for example, canola; tomato; eggplant; sweet and hot peppers; wheat; amaranth; barley; oat; rye; wild rice; walnut; pecan; brassica such as cabbage, broccoli, spinach; and various types of trees. The tractor T may be positioned in a field to drive along the rows of crop plants while supporting the pollen collection devices 10. The tractor T has a forward end and a rearward end and typically travels along the rows of plants in a forward direction. In the illustrated embodiment, the pollen collection devices 10 are mounted adjacent the forward end.

The tractor T comprises a carriage C configured to be driven along the rows of crop plants. A base B is attached to the carriage C. The base B has a width that is oriented transverse (e.g., generally perpendicular) to the forward direction of travel of the tractor T so that the base extends laterally outward from the tractor. The pollen collection devices 10 are mounted on the base B at spaced apart locations along the width of the base. Suitably, the pollen collection devices 10 are spaced apart along the width of the base B at intervals that correspond with the spacing of the rows of crop plants in the field so that each pollen collection device 10 may be generally aligned with one or more pollen-bearing rows of plants as the tractor T travels through the field. The tractor T may be driven at any suitable speeds for collecting pollen from the plants. In one embodiment, the tractor T travels at speeds from about 2 to about 5 mph during pollen collection. It will be understood that the tractor may travel at other speeds, such as speeds faster that 5 mph, without departing from the scope of the disclosure.

In the illustrated embodiment, the base B comprises a folding farm implement boom. In FIG. 1A, the boom B is shown in the unfolded or expanded configuration. As is known in the art, a folding boom can also be folded to a compact or folded configuration (not shown) in which the width of the base is narrow enough for the tractor T to drive on a road while supporting the pollen collection devices 10. In the illustrated embodiment, the tractor T comprises a high clearance farm tractor such as an applicator sold by Hagie Manufacturing Company of Clairon, Iowa. Other kinds of tractors or other kinds of vehicles or machines suitable for carrying the pollen collection devices 10 through a field may be used in other embodiments. For example, manned or unmanned aerial vehicles (e.g., drones), unmanned robots, etc., can be used to carry the pollen collection devices 10 in other embodiments. Although the illustrated embodiment shows four pollen collection devices 10, in other embodiments the base B can have any number of pollen collection devices 10 mounted thereon, including a single pollen collection device. Additionally, the pollen collection devices 10 can be mounted to the base B in other locations and at other spacing as needed for positioning along the rows of plants.

Referring to FIG. 1B, a pollen collection device 10 is configured to be moved through a row of plants P containing pollen to remove, dislodge or otherwise displace the pollen from the plants and collect the removed pollen for subsequent use. In the illustrated embodiment, the plants P are corn plants, such as sweet corn or grain corn. As such, the plants P include female flowers FF (e.g., corn silks) and male flowers MF (e.g., corn tassels). As is understood by those in the art, the male flowers MF produce pollen. The pollen from the male flowers MF of the plants P can be used to pollinate the female flowers of other plants such as in a cross-pollination process. The collected pollen may also be used for other pollination processes as well.

Figure 1C:
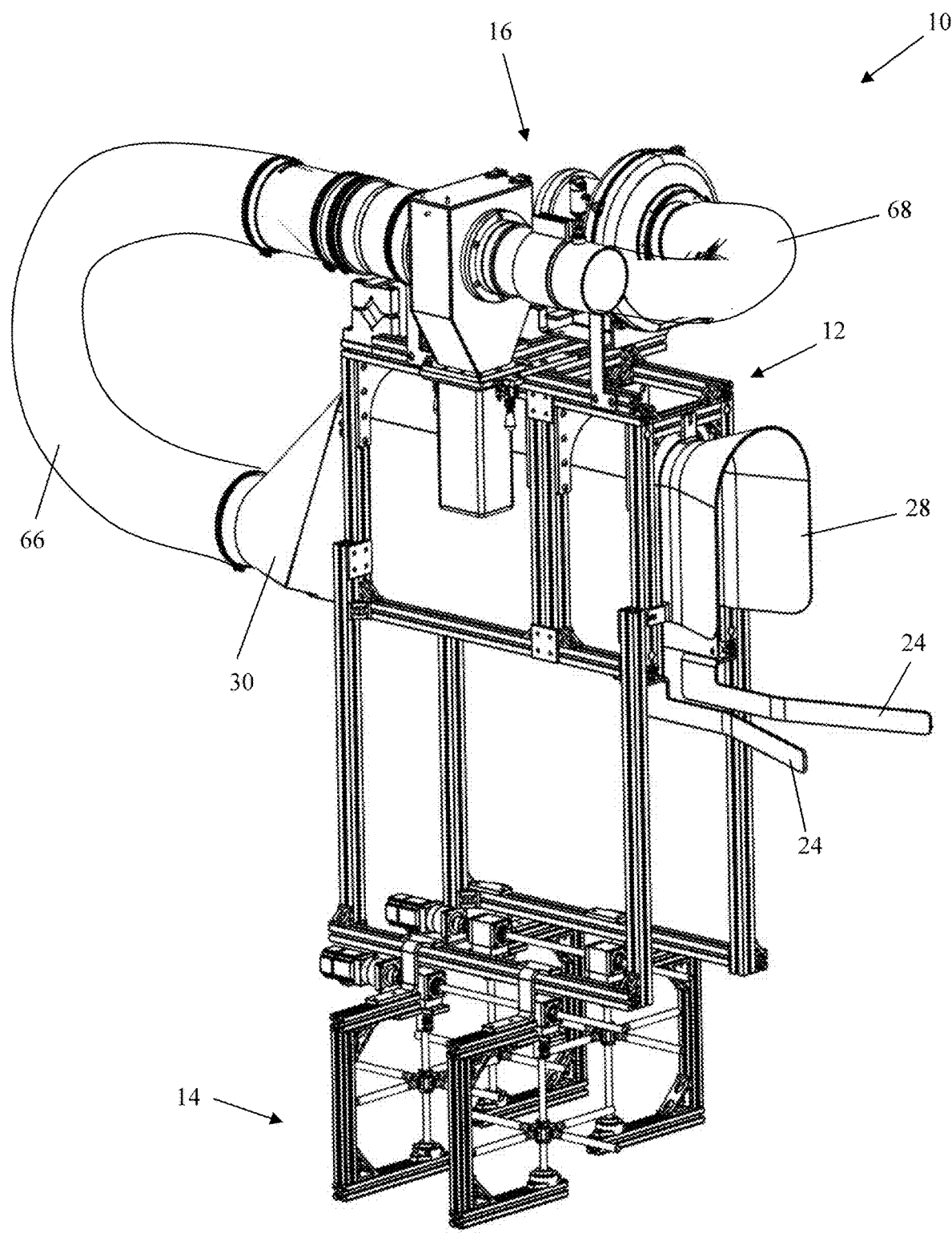
FIG. 1C is a perspective of the pollen collection device.
Figure 1D:
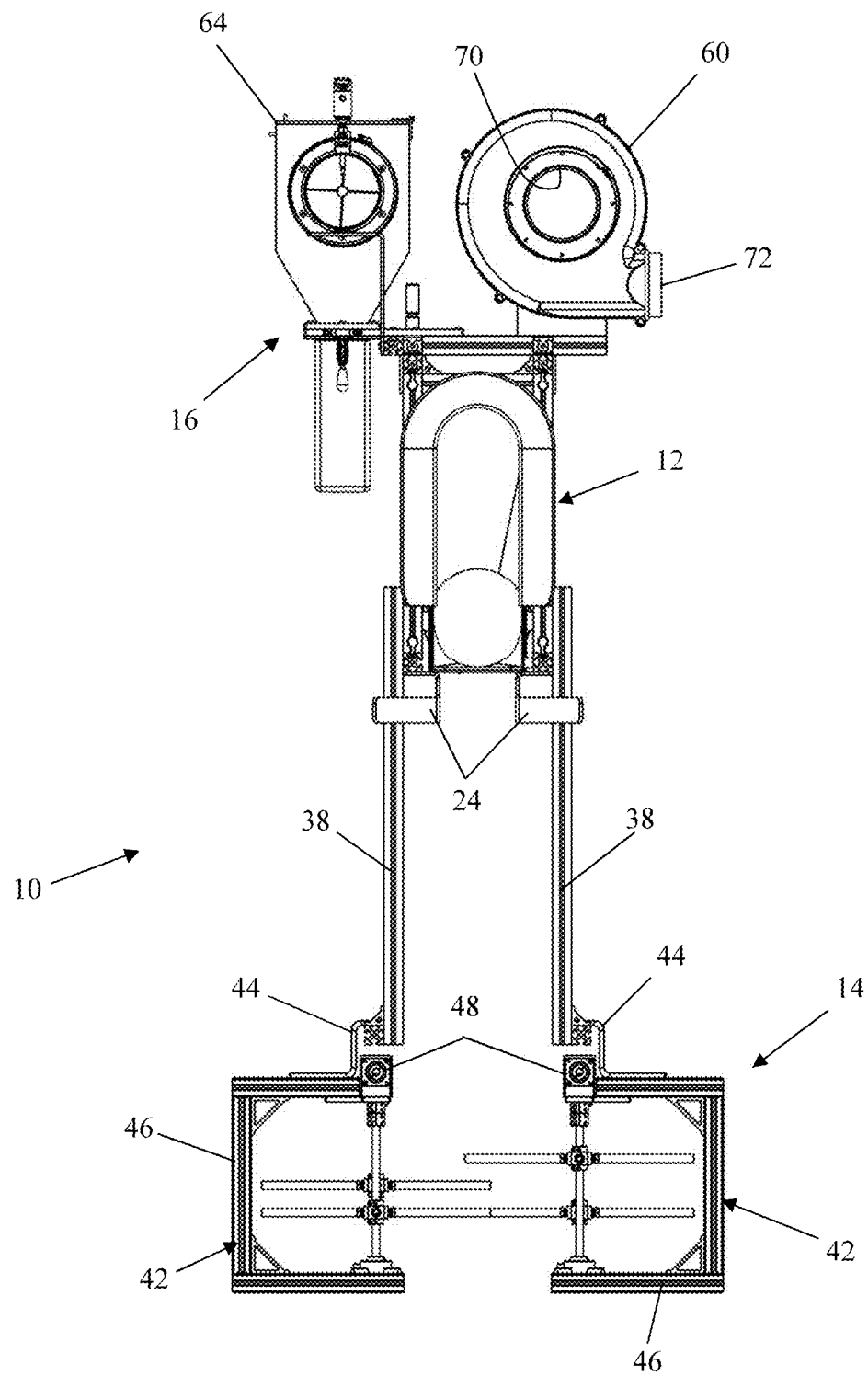
FIG. 1D is an end view of the pollen collection device.
Figure 2A:
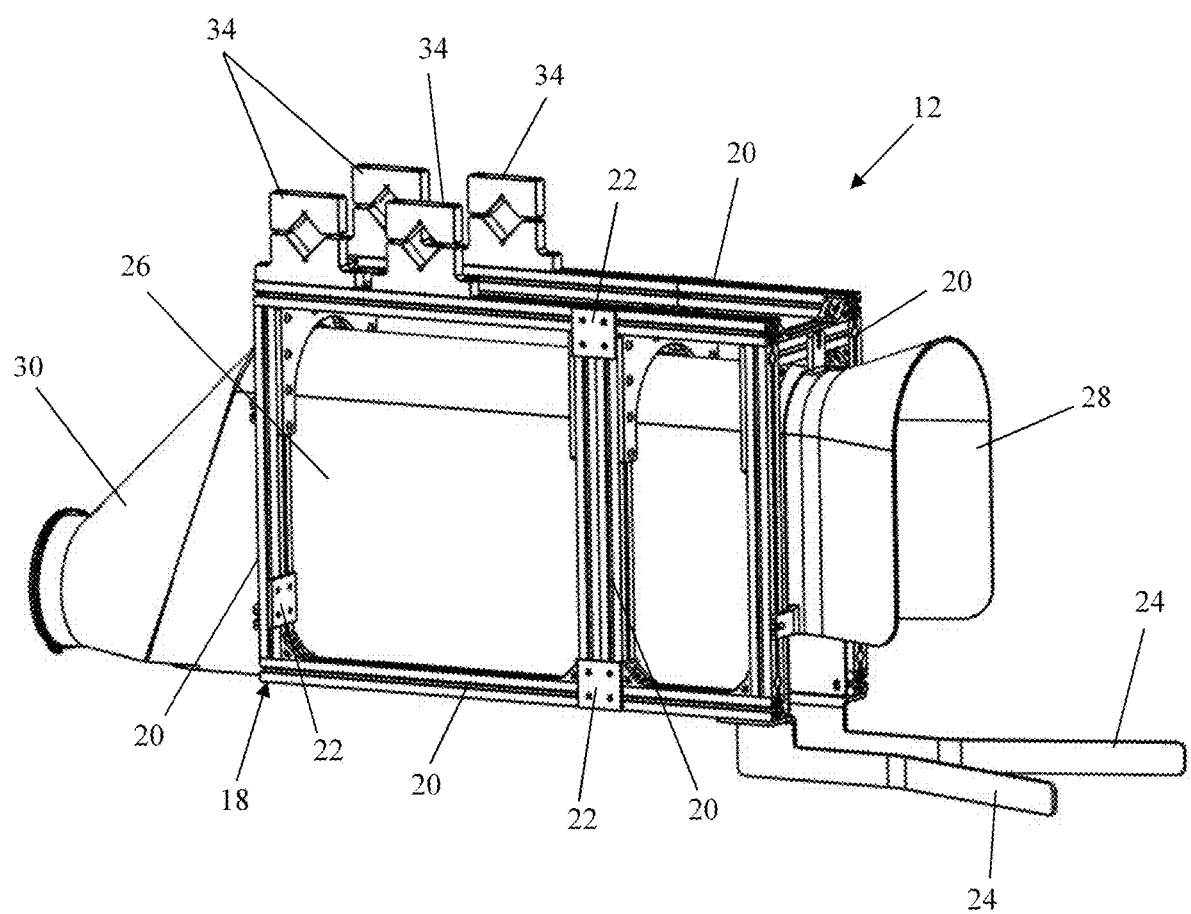
FIG. 2A is a perspective of a housing assembly of the pollen collection device.
Figure 2B:
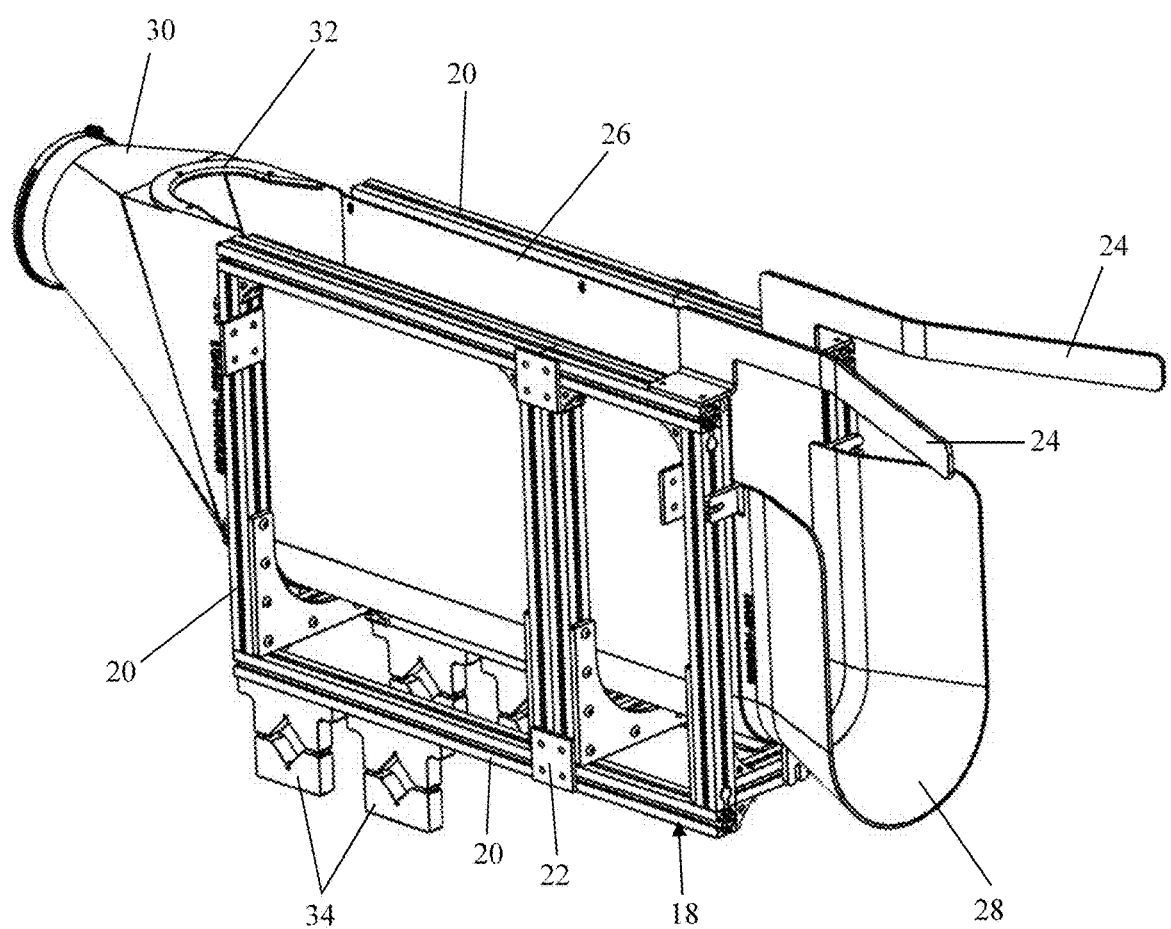
FIG. 2B is another perspective of the housing assembly.

Referring to FIGS. 1C and 1D, each pollen collection device 10 comprises a housing assembly 12 configured to receive and guide portions of the plants P through the pollen collection device, an agitation assembly 14 attached to the housing assembly and configured for agitating and advancing the plants through the pollen collection device for removing or displacing the pollen from the plants, and a pollen collection assembly 16 attached to the housing assembly and configured to collect the pollen removed from the plants. As will be explained in greater detail below, the pollen collection assembly 16 generates a force (e.g., a suction force) within the housing assembly 12 creating an air stream through the device 10 for drawing the pollen through the collection assembly to collect the pollen in the collection assembly and expel the air from the device for a continuous pollen collection process as the device is moved through the row of plants. The airstream may be created by other means such as by delivering a positive airflow through the device 10. Still other means for generating a pollen carrying force are also envisioned.

The housing assembly 12 may be used to mount the pollen collection device 10 to the base B on the tractor T. However, the collection device 10 may be supported on the tractor T in other ways without departing from the scope of the disclosure. Accordingly, the pollen collection device 10 allows for continuous collection of pollen as the device is moved through a row of crop plants. Therefore, the pollen collection device 10 facilitates efficient collection of pollen directly from the plant in the field. Moreover, the pollen collection assembly 16, through the use of the airstream generated by the suction force, provides a low impact method which maintains the quality of the pollen by substantially eliminating compaction forces on the pollen. As such, the pollen collected using the pollen collection device 10 is of a greater quality than the pollen collected through conventional pollen collection methods.

Referring to FIGS. 1C-2B, the housing assembly 12 comprises a frame 18 for supporting the components of the housing assembly. The frame 18 includes a plurality of frame members 20 connected together and defining an interior space. In the illustrated embodiment, the frame members 20 comprise elongate bars secured together by brackets 22. Configuring the frame 18 in this manner provides a modular construction allowing for the frame to be formed into different lengths by attaching additional or fewer sections of frame members 20 together. For example, additional frame members 20 can be connected together to form an extended length frame 18' (FIG. 11), or fewer frame members can be connected together to form a shorter length frame 18" (FIG. 12). The frame members 20 also provide for the top, bottom, sides, and ends of the frame 18 to be open. A pair of guides 24 are attached to the bottom of the frame 18 and extend forwardly from the frame. The guides 24 flare outward as they extend from the frame 18 to define a funnel for directing the plants P into the interior space of the frame 18. A main duct 26 is received within the interior space of the frame 18. The main duct 26 has an inverted U shape such that a bottom of the duct is open. The sides of the main duct 26 extend up along the sides of the frame 18 generally closing the open sides of the frame. The curved top of the main duct 26 similarly closes off the open top of the frame. The main duct 26 may be formed from a transparent material such as clear acrylic to provide visibility of the plants in the housing assembly 12. In one embodiment, the main duct 26 has a length from between about 24 and about 48 inches, a height of about 21 inches, and a maximum width of about 7 inches. In one embodiment, the main duct 26 has a length of about 36 inches. The main duct 26 can have other sizes and configurations without departing from the scope of the disclosure.

An inlet duct 28 is attached to a front end of the frame 18 and connects to a front section of the main duct 26 to provide a pathway from the inlet duct to the main duct. The inlet duct 28 has an inverted U-shaped opening, and a body section that tapers inward from the opening toward an opposite end of the inlet duct. The U-shaped opening and tapering profile of the inlet duct 28 facilitate delivering the tops of the plants P to the main duct 26. However, the inlet duct 28 could have other configurations without departing from the scope of the disclosure.

An outlet duct 30 is attached to a back end of the frame 18 and connects to a rear section of the main duct 26 to provide a pathway from the main duct to the outlet duct. A bottom of the outlet duct 30 has an opening 32 permitting the tops of the plants to exit the housing assembly 12 as the pollen collection device 10 is passed over the plants. A top of the outlet duct 30 tapers downward from a frame connection end to an opposite tube connection end. As will be explained in greater detail below, the configuration of the outlet duct 30 increases the time that the tops of the plants P are disposed within the main duct 26 and outlet duct for maximizing the pollen collection of the device 10. It will be understood that the outlet duct could have other configurations without departing from the scope of the disclosure. Moreover, although three separate duct sections are shown, a single unitary duct or some other number of duct sections could be incorporated without departing from the scope of the disclosure.

The housing assembly 12 also includes a plurality of clamps 34 attached to the frame 18. The clamps 34 may be fastened to the frame using fasteners (not shown). The clamps 34 are configured to clamp around a portion of the base B on the tractor T for mounting the pollen collection device 10 to the tractor. It will be understood that other means for attaching the pollen collection device 10 to the tractor T are envisioned within the scope of the disclosure.

Referring to FIGS. 1C, 1D, and 3A-3C, the agitation assembly 14 comprises a support frame 36 attached to the frame 18 of the housing assembly 12. The support frame 36 comprise a plurality of elongate support members including vertical support members 38 attached directly to the frame 18 of the housing assembly 12, and a pair of horizontal support members 40 attached to the vertical support members. An agitator unit 42 is mounted to each horizontal support member 40 by mounting brackets 44. Thus, the plants P pass between the two agitator units 42 for being contacted by the agitator units when the pollen collection device 10 is moved through the row of plants. Each agitation unit 42 comprises a pair of agitator frames 46, a motor 48 coupled to one of the agitator frames, a horizontal motor shaft 50 attached to the motor, a pair of gear assemblies 52 each connected to the horizontal motor shaft, a pair of vertical shafts 54 connected to respective gear assemblies, and two sets of arms 56 attached to respective vertical shafts.

Figure 3A:
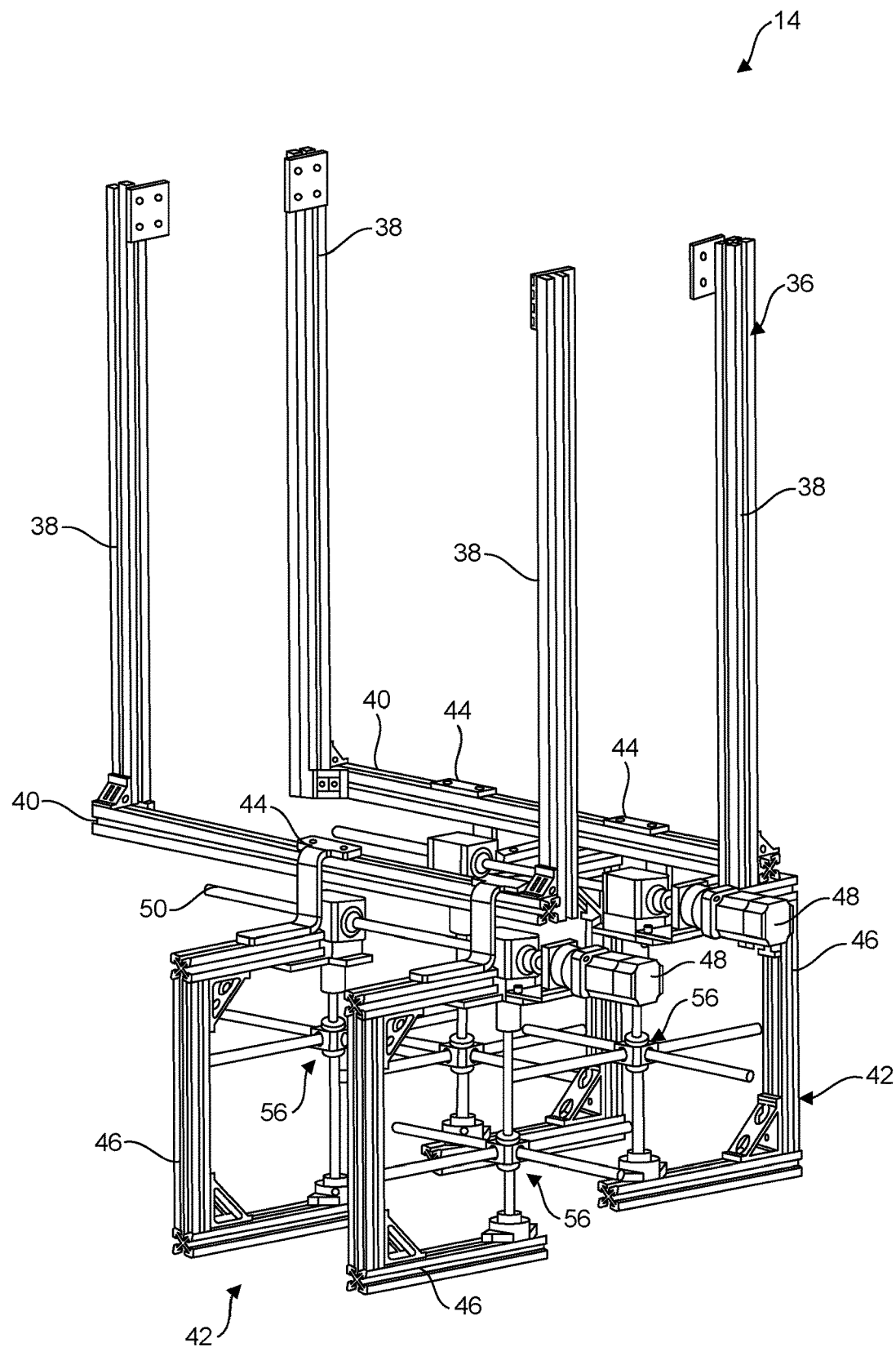
FIG. 3A is a perspective of an agitation assembly of the pollen collection device.
Figure 3B:
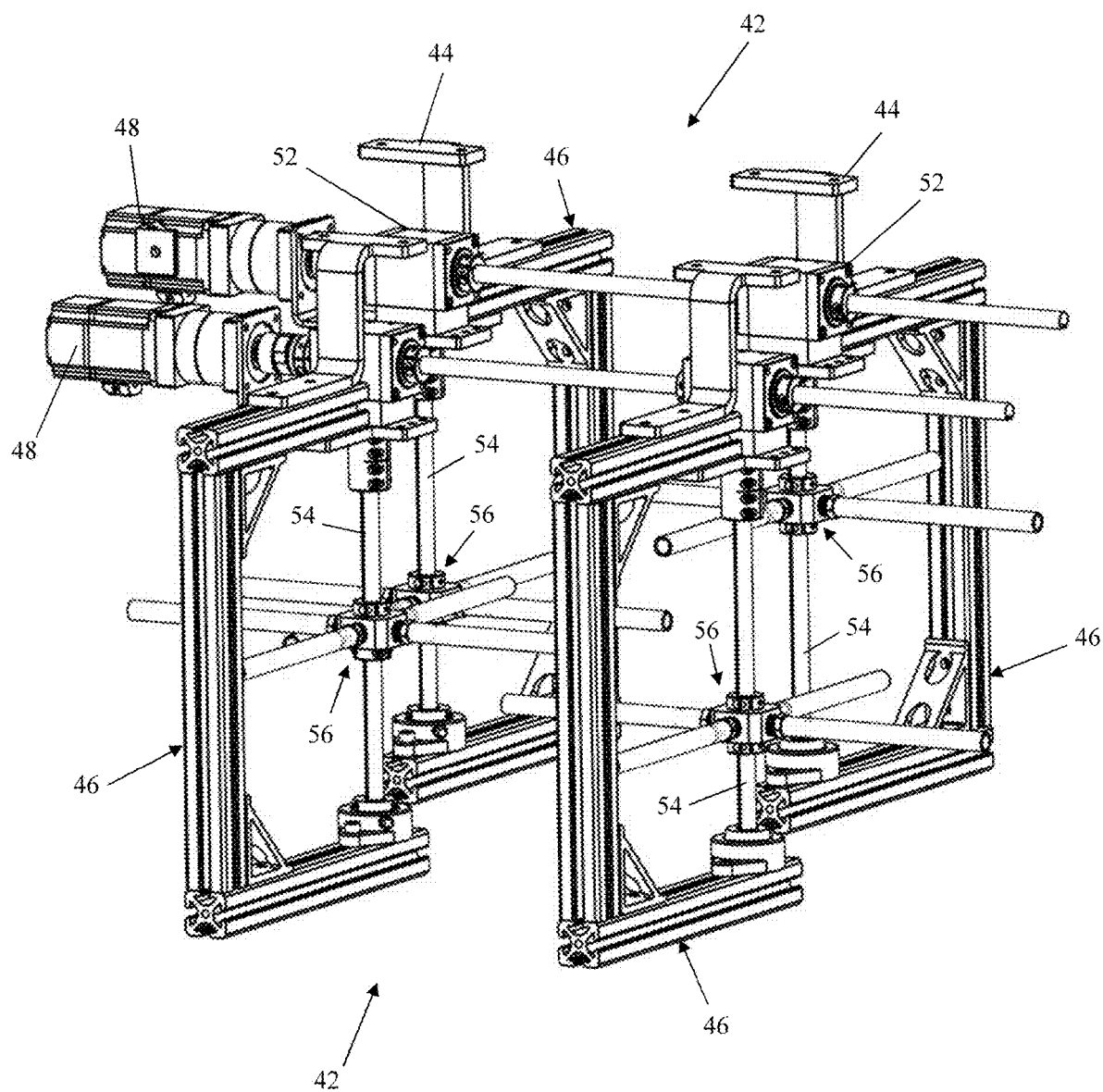
FIG. 3B is a perspective of agitation units of the agitation assembly.
Figure 3C:
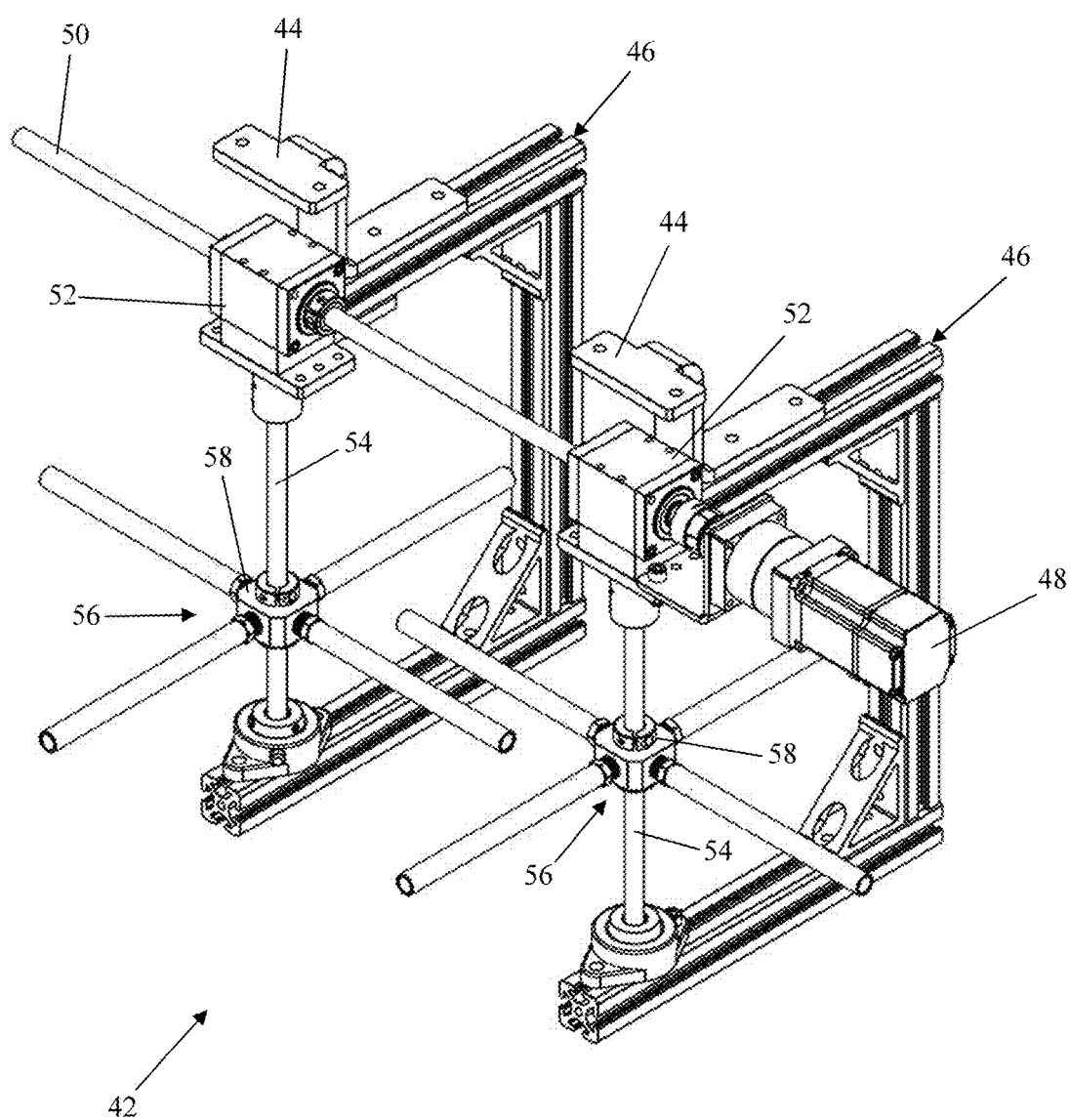
FIG. 3C is a perspective of one of the agitation units.

Operation of the motor 48 causes rotation to the arms 56 by way of the mechanical linkage between the horizontal motor shaft 50, gear assemblies 52, and vertical shafts 54. In particular, the motor 48 is oriented horizontally such that the horizontal shaft 50 is rotated about a horizontal axis. The gear assemblies 52 transfer the horizontal rotation of the horizontal shaft 50 to the vertical shafts 54 which in turn rotate about a vertical axis. The arms 56 are attached to and extend laterally from their respective vertical shafts 54. In the illustrated embodiment, there are four arms 56 attached to a vertical shaft 54 by a spindle 58 (FIG. 3C). The arms 56 are circumferentially spaced around the vertical shaft 54 and equally spaced apart from each other. Thus, actuation of the motor 48 causes the arms 56 to rotate about a vertical axis such the arms generally rotate within a horizontal plane. In one embodiment, one of the agitator units 42 is configured to rotate the two sets of arms 56 in a clockwise direction, and the other of the agitator units is configured to rotate the two sets of arms 56 in a counter clockwise direction. Thus, the rotation of the arms 56 can be in the same general direction as the relative movement of the plants P as the pollen collection device 10 is moved through the row of plants. Therefore, the arms 56 will hit the stalks of the plants P for agitating the plants to release the pollen from the plants as well as provide an advancement force to the plants to move the plants through the housing assembly 12. More particular, in one embodiment, the plants P are initially urged away from the interior space of the housing assembly 12 by the vertical support members 38 when the pollen collection device 10 is moved over the plants. However, the continued relative movement of the collection device 10 and the plants P causes the rotating arms 56 to contact the stalks of the plant to drive the plants into the interior of the housing assembly 12. These two counter forces may produce a whipping action at the tops of the plants P where the male flowers MF are located which can result in the displacing of the pollen from the plants. The motor 48 can be operated to rotate the arms 56 at any suitable rate. For example, the arms 56 may rotate at about 250 RPM. In one embodiment, the arms 56 rotate at a rate of between about 250 RPM and about 500 RPM.

In the illustrated embodiment, the arms 56 comprise hollow tubes. However, the arms could have other constructions without departing from the scope of the disclosure. Additionally, each agitation unit 42 includes a front set of tubes and a rear set of tubes. For a first agitation unit 42, the front set of tubes 56 is disposed at a first height, and the rear set of tubes 56 is disposed at a second height above the front set of tubes. For a second agitation unit 42, the front set of tubes 56 is disposed at a third height above the second height, and a rear set of tubes is disposed at the first height of the front set of tubes of the first agitation unit. Each set of tubes 56 is also staggered along the length of the agitation assembly 14. Therefore, the tubes 56 are free to rotate without contacting any tubes of another set. In one embodiment, the pollen collection device 10 is mounted such that the bottom-most set of tubes 56 are located less than about 30 inches from the ground. In one embodiment, the bottom-most set of tubes 56 are located between about 12 inches and about 26 inches from the ground. As will be explained in greater detail below, positioning the tubes 56 at these locations facilitates engaging the tubes with the stalks of the plants P. However, the tubes 56 could be located at other heights and positions without departing from the scope of the disclosure.

Additionally, it will be understood that rotation of the arms 56 could be imparted by other means without departing from the scope of the disclosure. The arms 56 could also rotate in other directions. For instance, both sets of arms 56 on the two agitator units 42 could rotate in the same direction, or each set of arms within a single agitator unit could rotate in opposite directions. In the illustrated embodiment, there are two agitation units 42. However, other numbers of agitation units could be used without departing from the scope of the disclosure. Further, each agitation unit 42 could have additional sets of rotating arms 56. Alternatively, a motor could be dedicated to each set of rotating arms 56. Still other configurations of the agitation assembly 14 are envisioned within the scope of the disclosure.

Referring to FIGS. 13 and 14, an alternative embodiment of an agitation assembly is generally indicated at 14'. The agitation assembly 14' includes a pair of rotating agitators 42' attached to a bottom of the housing assembly 12 on opposite lateral sides of the housing assembly. Each agitator 42' includes a plurality of bars 56' that extend longitudinally along the housing assembly 12'. In the illustrated embodiment, there are two bars 56' on each agitator 42'. However, any number of bars could be utilized. The bars 56' are operatively connected to a motor 48' through a gear and linkage assembly 52' for being rotated about a horizontal axis extending generally along the lateral sides of the housing assembly 12'. In one embodiment, the motor 48' effectuates the rotation of the two agitators 42' in opposite directions. Additionally, the bars 56' are offset from their rotational axis such that the bars 56' will pass under the interior space of the housing assembly 12' when they are rotated. Therefore, the bars 56' will contact the stalks of the plants when the pollen collection device 10' is moved over the row of plants. Thus, the bars 56' will agitate the plants to release the pollen from the plants like the agitation assembly 14 of the first embodiment. In one embodiment, the agitation assembly 14' has a targeted agitation of 12 impacts per plant. As shown in the figures, the orientation of the bars 56' on one of the agitators 42' is angularly offset from the orientation of the bars 56' on the other agitator. For example, the bars 56' of one agitator 42' are oriented 90 degrees out of phase with the bars 56' of the other agitator 42. So the bars will contact the plants in an alternating fashion knocking the plants back and forth between the agitators 42'. Alternatively, the agitation assembly 14' may include a single agitator having one or more bars for agitating the plants. Still other configurations of the agitation assembly 14' are envisioned.

Figure 4:
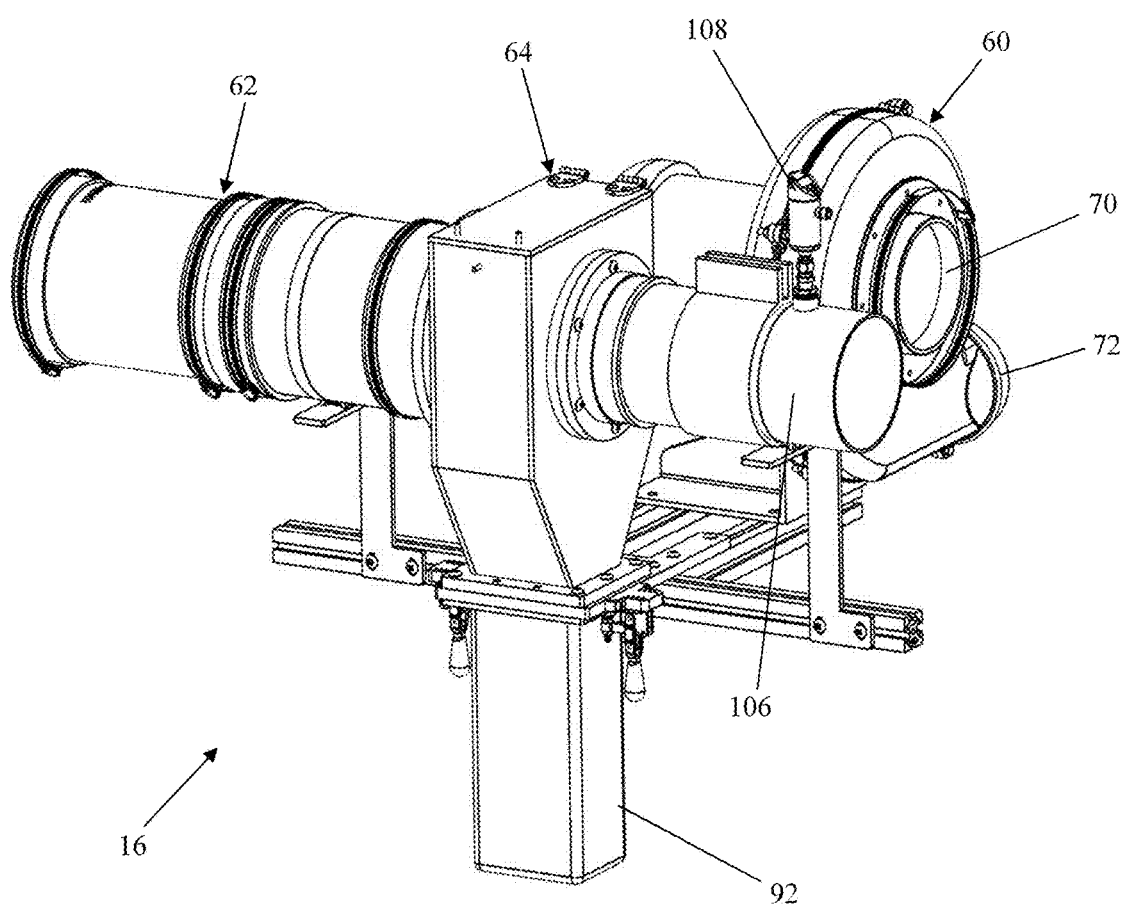
FIG. 4 is a perspective of a pollen collection assembly of the pollen collection device.
Figure 5:
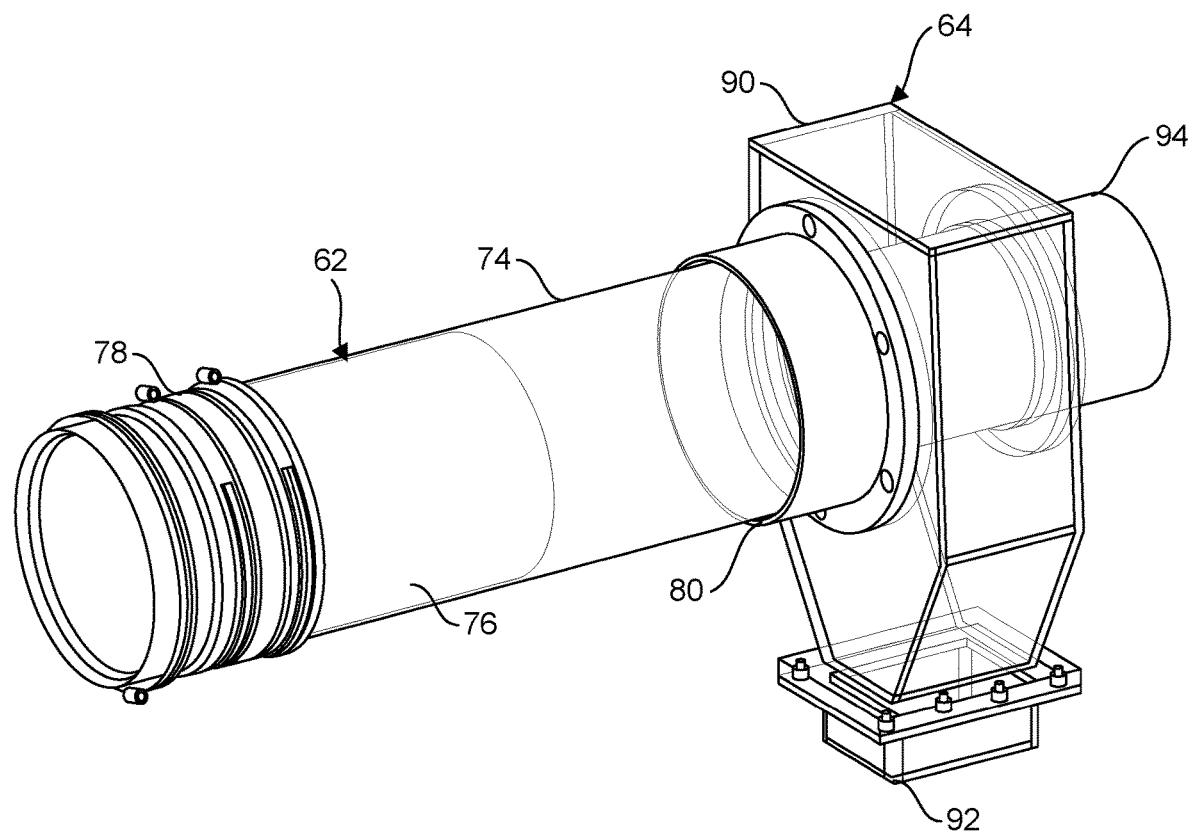
FIG. 5 is a perspective of a pollen diverter and pollen receiver of the pollen collection assembly.

Referring to FIGS. 1C, 4, and 5, the pollen collection assembly 16 comprises a blower 60 (broadly, an air handler) for generating an airflow through the pollen collection assembly, a diverter 62 for diverting the pollen within the collection assembly, and a receiver 64 attached to the diverter for receiving and collecting the diverted pollen. A first tubing 66 connects the diverter 62 to the outlet duct 30 of the housing assembly 12, and a second tubing 68 connecting the blower 60 to the receiver 64. Thus, an air passage extends through the pollen collection device 10 from the first tubing 66, through the pollen collection assembly 16, into the second tubing 18 and to the blower 60. The blower is configured to generate an airstream within the air passage that draws the pollen, which has been separated from the plants using the agitation assembly 14, from the housing assembly 12, through the first tubing 66, through the diverter 62, and into the receiver 64. The second tubing 68 provides a passage for the pollen-free air to be expelled from the collection assembly 16 and through the blower 60 to the surrounding atmosphere. Therefore, the pollen collection assembly 16 continuously separates the pollen from the air stream as the pollen collection device 10 is moved through a row of plants. Further, the diverter 62 eliminates clogging within the device 10 and the need for replacement. Additionally, the diverter substantially eliminates the compaction forces on the pollen that conventional pollen collection methods employ. Thus, the pollen collection assembly 16 maintains the quality of the pollen after collection which increases the germination rate of the pollen in subsequent pollination processes.

The blower 60 comprises an air inlet 70 and an air outlet 72. The air inlet 70 is connected to the second tubing 68 and the air outlet 72 is in communication with atmosphere. Operation of the blower 60 to blow air out of the air outlet 72 draws a suction at the air inlet 70 which generates an air flow through the air passage in the pollen collection assembly 16 and the interior of the housing assembly 12. Therefore, the pollen that is displaced or removed from the plants P in the housing assembly 12 is carried through the air passage by the air flow generated by the blower 60. In one embodiment, the blower 60 creates a volumetric flow rate of at least about 500 CFM within the air passage through the pollen collection device 10. In a preferred embodiment, the blower 60 creates a volumetric flow rate of about 600 CFM. In one embodiment, the blower 60 creates a volumetric flow rate between about 400 and about 600 CFM. The blower may create other volumetric flow rates. A terminal velocity of the pollen traveling through the air passage may be about 7 m/s. The pollen may travel through the device at a speed from at least about 2 m/s, and in one example, from about 2 m/s to about 25 m/s, or from about 2 m/s to about 11 m/s. However, the pollen may travel at other rates without departing from the scope of the disclosure. It has been found that pollen traveling at the disclosed rates through the pollen collection assembly 16 provides a low impact collection process which maintains the viability and health of the pollen.

Figure 6:
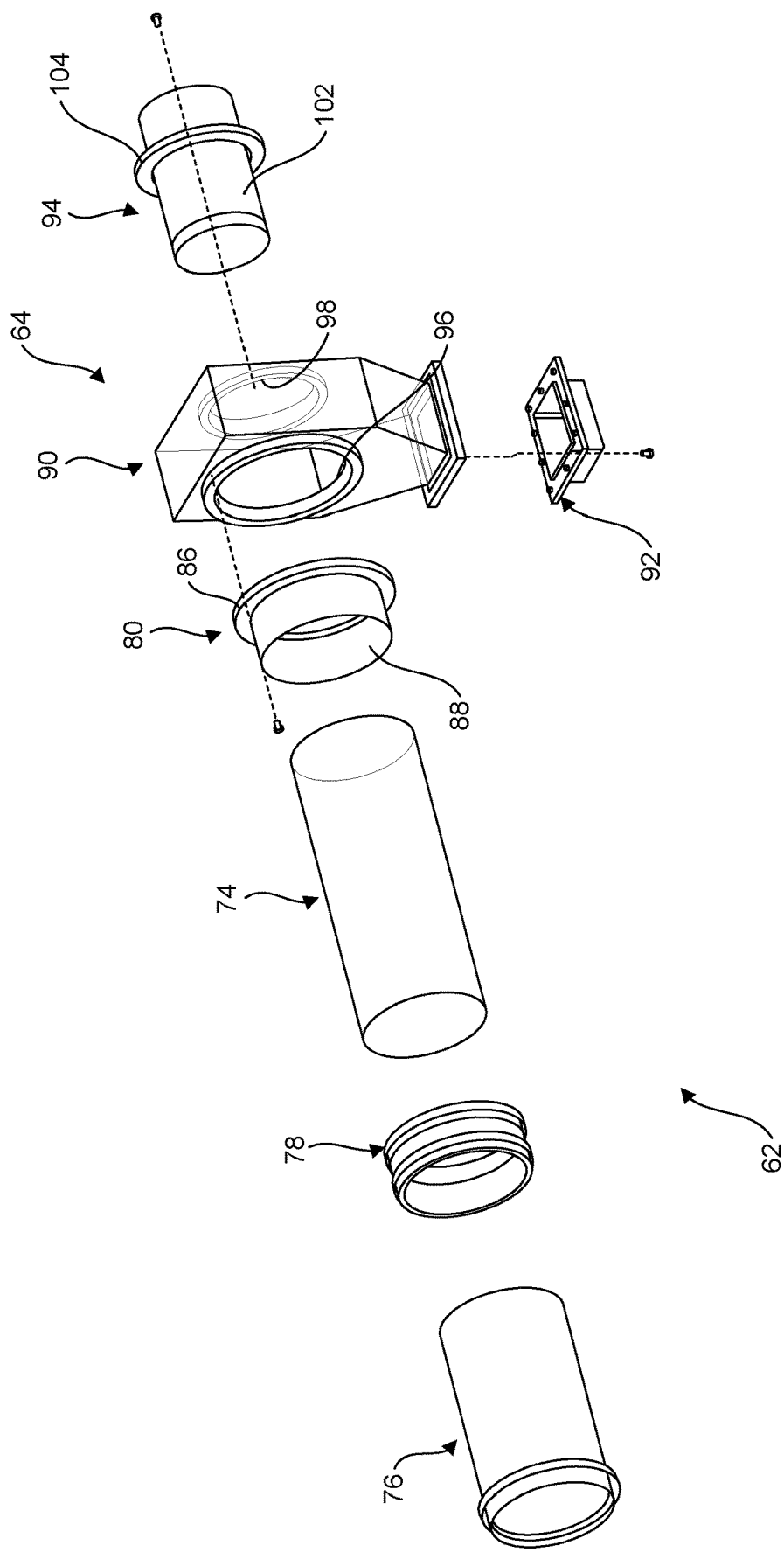
FIG. 6 is an exploded view of the pollen diverter and pollen receiver.

Referring to FIGS. 4-6, the diverter 62 comprises a housing 74 (e.g., a cylindrical housing or a housing having a different shape), a vane insert 76 received in a first end of the cylindrical housing, an adapter 78 received around the first end of the cylindrical housing to retain at least a portion of the vane insert in the cylindrical housing, and an inlet fitting 80 attached to a second end of the cylindrical housing for attaching the diverter to the receiver 64. The vane insert 76 may be slidable within the first end of the cylindrical housing 74 for selectively positioning the vane insert inside the cylindrical housing. The cylindrical housing 74 has a sufficient length to properly position the vane insert 76 from the receiver 64. An inner diameter of the cylindrical housing 74 is sized to receive the vane insert 76 in the first end of the cylindrical housing. An outer diameter of the cylindrical housing 74 is sized for reception in the inlet fitting 80. In one embodiment, the outer diameter of the cylindrical housing 74 is about 8 inches. However, other dimensions of the cylindrical housing 74 can be utilized. The adapter 78 is configured to fix the position of the vane insert 76 within the cylindrical housing 74. Thus, the vane insert 76 does not rotate or otherwise move within the cylindrical housing 74 during use.

Figure 7A:
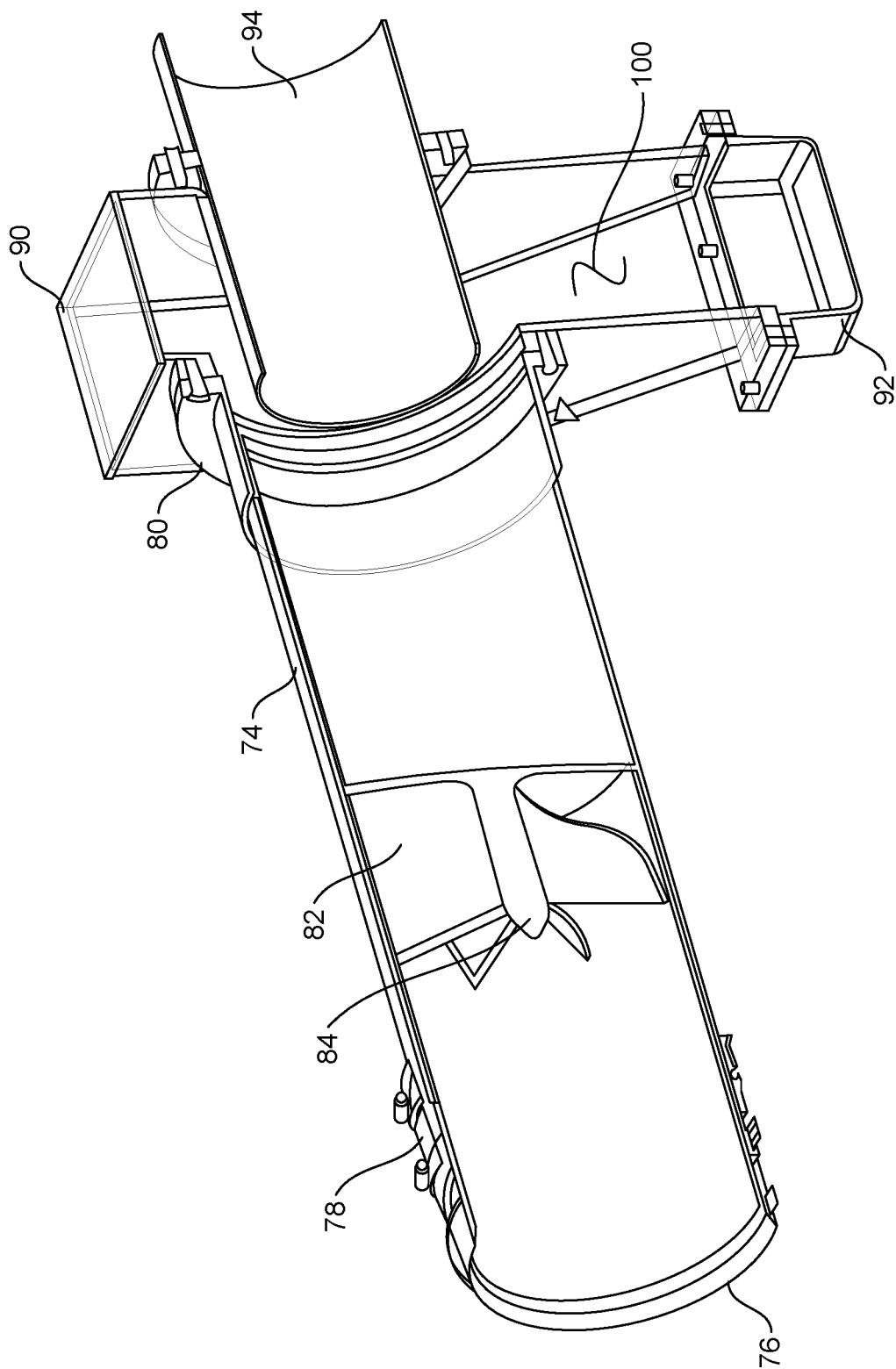
FIG. 7A is section of the pollen diverter and pollen receiver.

Referring to FIG. 7A, the vane insert 76 comprises a cylindrical or semi-cylindrical member including vanes 82 arranged within an interior of the cylindrical member. The vanes 82 are formed around a hub 84 extending longitudinally within the cylindrical member. The vanes 82 and hub 84 may be broadly considered a vane assembly. In the illustrated embodiment, the vanes 82 extend helically around the hub 84 from adjacent one end of the hub to an opposite end of the hub. However, the vanes need not extend helically around the hub so long as the vanes impart rotation to the airstream. Thus, non-helical assemblies may be used. Further, as the vane insert 76 does not rotate in the cylindrical housing 74, the vanes 82 also remain stationary in the housing and do not rotate or otherwise move relative to the remainder of the cylindrical member of the vane insert. As will be explained in greater detail below, the vanes 82 are configured to direct the pollen in the air passage radially outward by inertial force toward the inner surface of the cylindrical housing 74 for eventual collection by the receiver 64.

The inlet fitting 80 comprises an annular flange 86 for attaching the inlet fitting to the receiver 64, and a tubular extension 88 projecting from the annular flange for receiving the second end of the cylindrical housing 74. The tubular extension 88 may be secured to the cylindrical housing 74 by any suitable means. For example, the cylindrical housing 74 may be press fit into the tubular extension 88 and/or adhesive may secure the tubular extension to the cylindrical housing. In one embodiment, the internal diameter of the tubular extension 88 of the inlet fitting 80 is about 8 inches. The inlet fitting 80 may have other configurations without departing from the scope of the disclosure. Moreover, the inlet fitting 80 could be omitted such that the cylindrical housing 74 is directly attached to the receiver 64. For instance, an annular flange (not shown) could be formed on the cylindrical housing 74 for attachment to the receiver 64. Still other means for attaching the diverter 62 to the receiver 64 are envisioned.

Figure 7B:
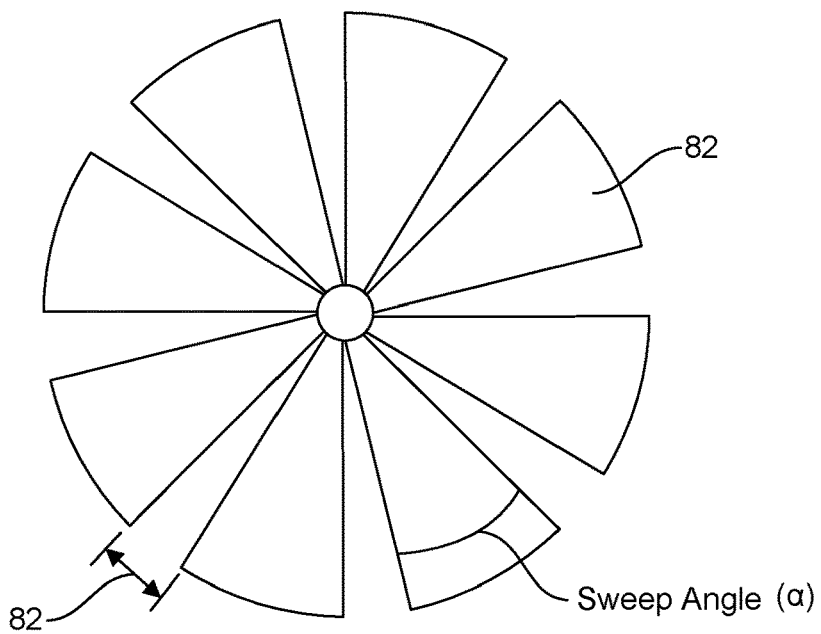
FIG. 7B is an end view of a vane assembly of the pollen diverter.
Figure 7C:
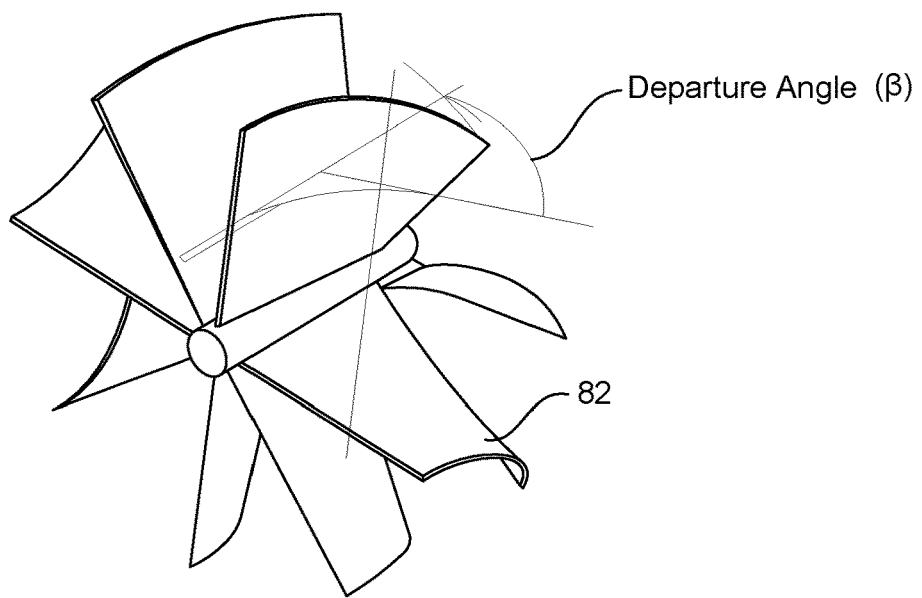
FIG. 7C is a perspective of the vane assembly.
Figure 10A:
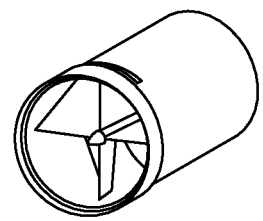
Figure 10D:
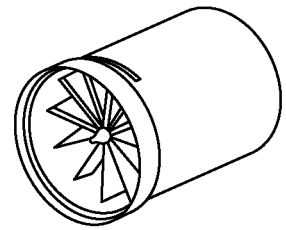
Figure 10B:
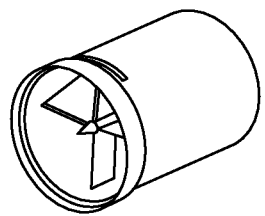
Figure 10E:
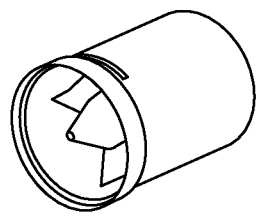
Figure 10C:
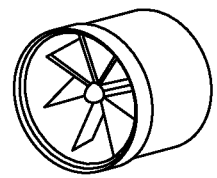
Figure 10F:
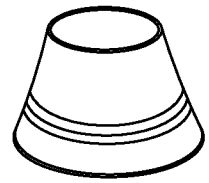

In the illustrated embodiment, there are four vanes 82 in the diverter 62. However, any number of vanes 82 can be used without departing from the scope of the disclosure. The vane length may also vary. In one embodiment, a length of the vanes 82 is about 4 inches. Further, as mentioned above, the position of the vanes 82 can be adjusted by moving the vane insert 76 within the cylindrical housing 74. In one embodiment, an end of the vanes 82 is disposed between about 16 and about 20 inches from the second end of the cylindrical housing 74 attached to the receiver 64. The geometry and shape of the vanes 82 may also vary. In one embodiment, the vanes 82 have about a 40-degree sweep angle α, about a 60-degree departure angle β, and about a 1-inch annular gap 83 (FIGS. 7B and 7C). Referring to FIG. 10, a number of alternative vane insert configurations are shown. For example, the vanes may comprise a long helix where the vanes complete a full helical sweep around the hub (FIG. 10A), a short helix where the helical pitch has been reduced to provide a more aggressive curvature (FIG. 10B), an aggressive sweep where the vane length has been decreased to provide a more aggressive curvature (FIG. 10C), a helix vortex where the number of vanes is increased to 12 (FIG. 10D), or an alternative helix vortex (FIG. 10E). Moreover, the vane inserts are interchangeable. Therefore, an operator can select a particular vane insert for a desired use. An outlet adapter (FIG. 10F) can also be utilized to minimize the air velocity within the receiver 64 and promote settling. A flange on the outlet adapter is configured to reduce the annular gap between the inlet and outlet ducts.

Referring to FIGS. 4-7A, the receiver 64 comprises a collection box 90 for receiving the pollen diverted by the diverter 62, a pollen bucket 92 removably attached to the collection box for storing the pollen collected by the collection box, and an outlet fitting 94 attached to the collection box 90 for carrying the substantially pollen free airstream through the collection box to the second tubing 68 for removal from the pollen collection assembly 16. As will be explained in greater detail below, the receiver 64 is positioned and configured to collect and store the pollen removed from the plants P while allowing the airstream to pass through the receiver and out of the pollen collection assembly 16. Thus, the pollen collection assembly 16 can continuously collect pollen from the plants P as the pollen collection device 10 is moved through the row of plants.

The collection box 90 comprises a housing defining an inlet opening 96 in communication with the diverter 62, an outlet opening 98 in communication with the outlet fitting 94, and an interior 100 between the inlet opening and outlet opening. A depth of the collection box 90 extends between a front wall defining the inlet opening 96 and a rear wall defining the outlet opening 98. The depth of the collection box 90 may be sufficiently deep to substantially prevent the pollen entering the collection box from contacting the rear wall. In one embodiment, the depth of the collection box 90 may be between about 4 and about 6 feet deep. However, other depths for the collection box 90 are envisioned without departing from the scope of the disclosure. The collection box 90 has an open bottom in communication with the pollen bucket 92 attached to the open bottom of the collection box. The pollen bucket 92 comprises a receptacle including an open top to place the interior 100 of the collection box 90 in communication with an interior of the pollen bucket. The outlet fitting 94 comprises a tubular member 102 and an annular flange 104 extending around the tubular member. The annular flange 104 is disposed between longitudinal ends of the tubular member 102 forming an inlet portion extending through the collection box 90 and an outlet portion extending away from the collection box. The inlet portion of the tubular member 102 is received within the outlet opening 98 in the collection box 90, and the annular flange 104 attaches to an exterior surface of the collection box to secure the outlet fitting 94 to the collection box. The outlet portion of the outlet fitting 94 connects to the second tubing 68. A clamp 106 (FIG. 4) may be used to secure the second tubing 68 to the outlet portion of the outlet fitting 94.

Figure 8:
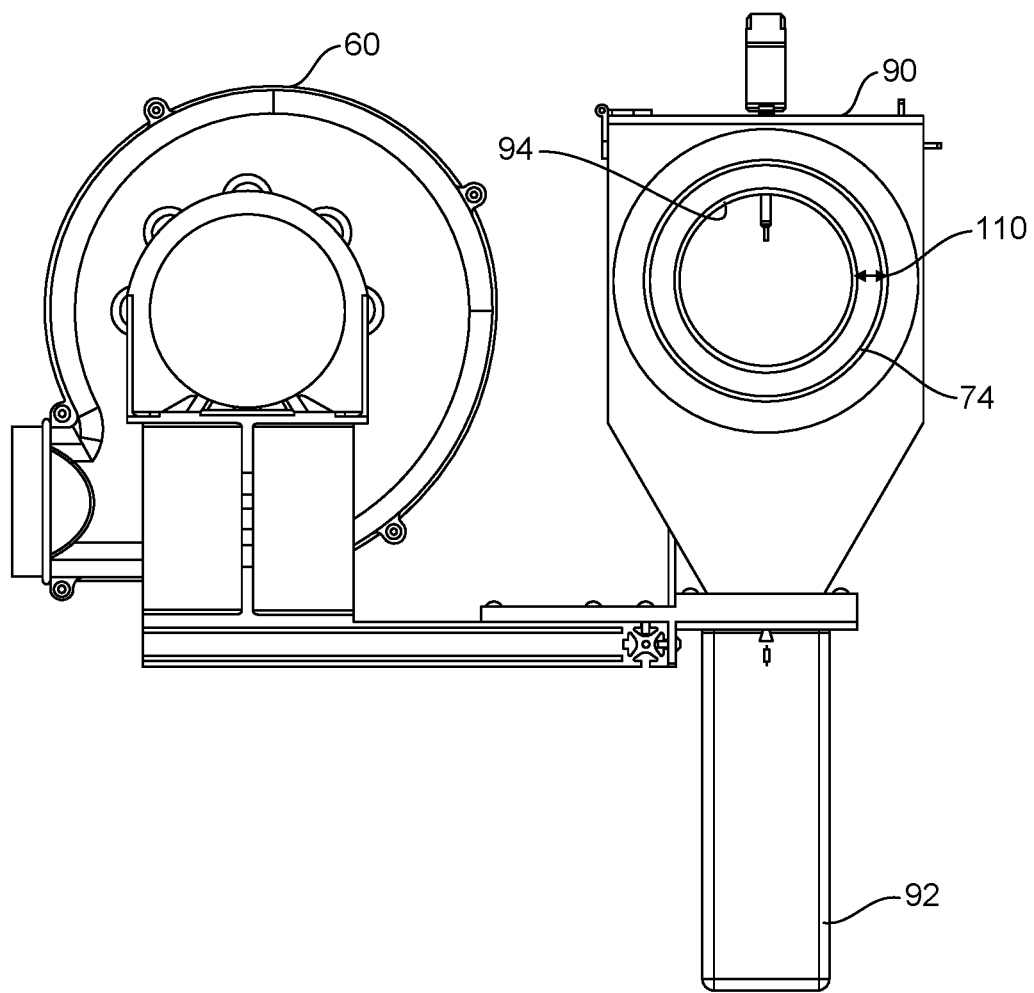
FIG. 8 is another section of the pollen diverter and pollen receiver.

A flow sensor 108 (FIG. 4) may also be attached to the second tubing 68 for monitoring fluid flow through the second tubing. It will be understood that flow sensors can be located at other positions on the device 10 to monitor fluid flow. The sensor 108 may also measure temperature within the flow passage. Alternatively, a separate sensor may be used to measure temperature. Additionally, the pollen bucket 92 can be replaced with a pollen storage device (not shown) that creates a storage environment having optimal temperature, humidity, and airflow. A large pollen bucket 92 is shown in FIGS. 4 and 8, and a small pollen bucket 92 is shown in FIGS. 5-7A. Other configurations for storing the pollen are envisioned. Additionally or alternatively, continuous systems for the separation of anthers and other debris from the pollen can be attached to the receiver 64.

A suitable method of using the pollen collection device 10 to collect pollen from crop plants will now be briefly described. The method described below is specifically directed toward the collection of pollen from corn plants. However, the same techniques can be employed in collecting pollen from other types of crops. As explained above, and with reference to FIG. 1A, the illustrated pollen collection devices 10 are spaced apart along the width of the base B of the tractor T to collect pollen from rows of pollen-bearing corn plants P. All of the plants in the field are grown until the pollen-bearing corn plants P bear pollen suitable for pollination.

After the plants P are grown such that they bear pollen suitable for pollination, an operator installs the pollen collection devices 10 on the tractor T. The operator may, for example, measure or visually inspect the heights of the plants P and adjust the height of the housing assembly 12 so that the housing assembly is arranged for receiving the male flowers MF within the main duct 26 of the housing assembly. Additionally or alternatively, the operator may position the pollen collection device 10 such that the arms 56 of the agitation assembly 14 are disposed at a predetermined height above the ground (e.g., about 26 inches) consistent with the arms engaging the stalks of the plants P for agitating the plants. The heights of the pollen collection devices 10 may also be automatically adjusted through use of the sensors, controller, and the actuators (e.g., hydraulic pistons) mounted on the tractor T.

In use, the tractor T can be driven through a field of corn plants P along a row of plants. The operator initially activates the blower 60 to create a suction airstream through the device 10. Thus, an air stream flows from the housing assembly 12, through the first tubing 66, through the pollen collection assembly 16, into the second tubing 68, and out through the blower 60. The motors 48 of the agitation assembly 14 may also be activated to begin rotation of the arms 56 on the agitation units 42. With the pollen collection device 10 configured so a suction force is created in the main duct 26 of the housing assembly, and the agitation assembly 14 activated, the operator drives the tractor T such that the pollen collection devices 10 pass through the rows of plants P. As a pollen collection device 10 moves through a row of plants P, the guides 24 funnel the tops of the plants toward the interior space of the housing assembly 12. After passing through the guides 24, the plants P are initially urged away from the interior space of the housing assembly 12 by the vertical support members 38. However, the continued advancement of the collection device 10 through the plants P causes the rotating arms 56 of the agitation assembly 14 to contact the stalks of the plant to drive the plants into the interior of the housing assembly 12. These two counteracting forces produce a whipping action at the tops of the plants where the male flowers MF are located which can result in the displacing of the pollen from the plants. Continued movement of the housing assembly 12 over the plants P moves the outlet duct 30 into registration with at least a portion of the plants. The angled shape of the outlet duct 30 bends the tops of the plants P back toward the main duct 26 so that even when the stalks and lower parts of the plants move out from under the main duct, the tops of the plants will remain within the main duct for at least a period of time. This maximizes the time the plants P, and in particular the tops of the plants, are contained within the main duct 26 to increase the time for the capturing the displaced pollen within the main duct. It will be understood that for the embodiment shown in FIG. 13, the bars 56' will rotate to contact the stalks of the plants P to displace the pollen from the plants.

Figure 9:
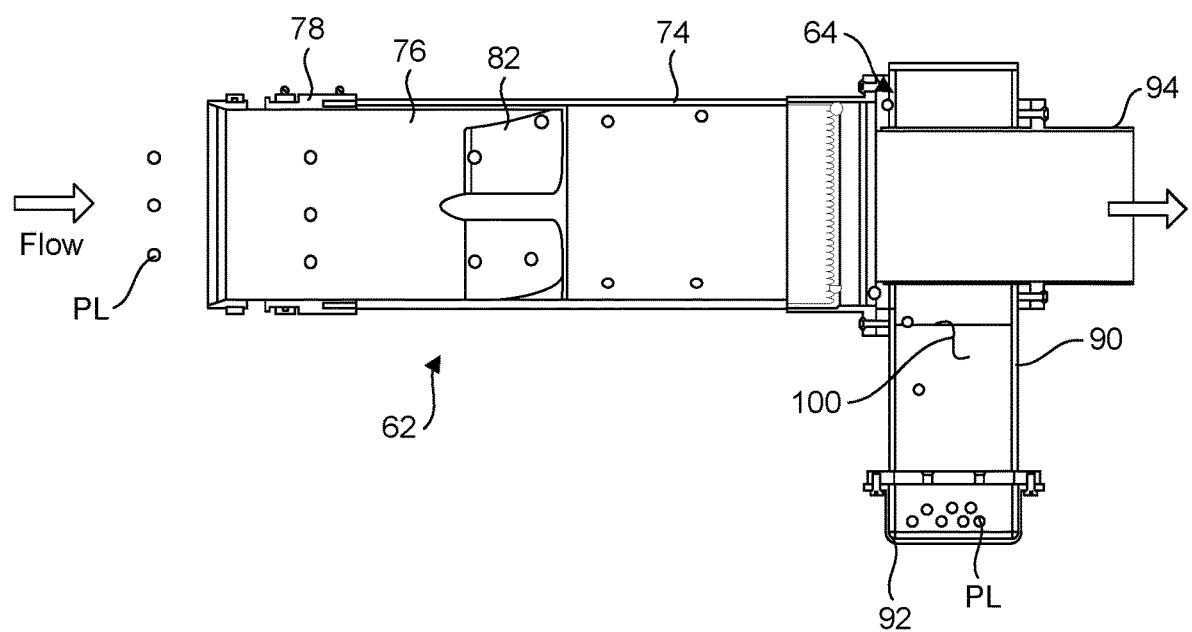
FIG. 9 is an illustration of pollen traveling through the pollen diverter and into the pollen receiver.

The displaced pollen is then temporarily held within the main duct 26 of the housing assembly 12. The airstream in the pollen collection device 10 carries the pollen in the housing assembly 12 out of the outlet duct 30, through the first tubing 66 and into the diverter 62 of the pollen collection assembly 16. Referring to FIG. 9, the vanes 82 of the diverter 62 impart rotation to the airstream flowing through the diverter to divert the pollen PL and other particulates in the airstream radially outward as the pollen travels longitudinally through the diverter. Thus, pollen PL traveling generally along the longitudinal axis of the diverter 62 will be forced radially outward by the vanes 82 upon passing through the vane inert 76. Therefore, as the pollen PL exits the vane insert 76 and continues to travel along the airstream through the cylindrical housing 74, the pollen will travel generally along the inner wall of the cylindrical housing. As such, when the pollen PL reaches the second end of the cylindrical housing 74, the pollen is able to pass through an annular gap or clearance 110 (FIG. 8) between an outer surface of the inlet portion of the outlet fitting 94 and the inner wall of the cylindrical housing. The pollen PL then flows into the collection box 90 of the receiver 64. The space within the collection box 90 surrounding the inlet portion of the outlet fitting 94 comprises dead air through which the airstream created by the blower 60 does not flow. Thus, once the pollen PL reaches the dead air space within the collection box 90, the movement of the pollen along the direction of the airstream slows down until the pollen eventually stops moving in the airstream direction. At this point the pollen drops into the collection box 90 where the pollen eventually falls to the bottom of the collection box and into the pollen bucket 92 where the pollen is stored for subsequent removal. By diverting the pollen PL from the airstream into the dead air space of the receiver 64, the impact of the pollen during the collection process is minimized and thus the health of the pollen is preserved. In one embodiment, the pollen collection device 10 has a 100% efficiency such that all of the pollen that travels through the collection assembly 16 is collected within the receiver 64. In one embodiment, the pollen collection device 10 has at least a 60% efficiency. Still other levels of efficiency are envisioned without departing from the scope of the disclosure. Additionally or alternatively, the pollen can be directed into any number of intermediate systems prior to storage. For example, the pollen could be directed to a debris removal system.

Finally, the pollen-free airstream continues to flow out of the receiver 64 and into the second tubing 68 for being expelled from the pollen collection device 10 through the blower 60. Thus, the pollen collection device 10 creates a continuous airstream which carries the displaced pollen from the plants P into the receiver 64 as the collection device travels along a row of plants while permitting the airstream to exit the device. Therefore, the pollen collection device 10 can efficiently collect pollen from the plants P while providing minimum impact or damage to the pollen as compared to conventional pollen collecting methods.

Referring to FIG. 15, a pollen collection device of another embodiment is generally indicated at 10'''. The pollen collection device can be installed on a tractor, detasseler, or sprayer and passed over a row of plants like pollen collection devices 10 and 10' of the previous embodiments. Additionally, the pollen collection device 10'' incorporates an automated and standardized process to efficiently collect pollen from the plants and precisely quantify the volume of pollen collected and analyze the quality of the collected pollen. This information can then be used to provide production estimations and enable the identification of certain pollen production conditions that may optimize pollen production and/or viability during subsequent planting. Thus, the plants with the most viable pollen can be planted and harvested for seed production. Therefore, the pollen collection device 10''' can be used to improve the genetics of the pollen lines.

The pollen collection device 10''' is configured similarly to pollen collection device 10' and thus operates to collect pollen in the same manner as pollen collection device 10'. Additionally, the pollen collection device 10''' can be used for research purposes to evaluate the quality and quantity of the pollen collected using different treating and testing methods. In the illustrated embodiment, the pollen collection device 10''' comprises a housing assembly 12''' configured to receive and guide portions of the plants through the pollen collection device, an agitation assembly 14''' attached to the housing assembly and configured for agitating and advancing the plants through the pollen collection device for removing or displacing the pollen from the plants, and a pollen collection assembly 16''' attached to the housing assembly and configured to collect the pollen removed from the plants in a collection chamber 90'''.

The pollen collection device 10''' further comprises one or more measurement/sensor devices to measure various characteristics of the collected pollen. The measurement/sensor devices are shown schematically in FIG. 15. In one embodiment, the pollen collection device 10''' includes a scale 120''' for measuring a weight of the pollen collected in the collection chamber 90''', a volume sensor 122''' for measuring a volume of the pollen in the collection chamber, an NIR or capacitance sensor 124''' for detecting a moisture content of the pollen in the collection chamber, a viability sensor 126''' for detecting the pollen's ability to effect fertilization and development of the seed, a location sensor 128''' for collecting location data to track the location of the plot from which the pollen was collected, a timing sensor 130''' (broadly, a timer) for monitoring the time at which the pollen was collected, and a flow camera 132''. These measurement/sensor devices allow the pollen collection device 10''' to provide a quality estimation of the collected pollen. The estimation of pollen quality can aide in the identification of the preferred conditions and locations for plant growth to produce the most desirable pollen for seed development. It will also be understood that other devices could be used without departing from the scope of the disclosure. For example, a refrigeration unit 134''' could be connected to the collection chamber 90''' to preserve and store the pollen after it has been collected. Additionally, a sieve unit 136''' could be connected to the collection chamber to separate unwanted particles and debris from the collected pollen. Still other attachment devices are envisioned without departing from the scope of the disclosure.

In one embodiment, the collection chamber 90''' is changed after the pollen collection device 10''' is moved to a new plot. For example, an automated apparatus (not shown) may be used to change the collection chamber 90'''. The automated apparatus can also be used for sample identification of the collection chamber 90'''.

In one embodiment, the pollen collection devices of the present disclosure can be used in a controlled environment, such as in breeding trials in a cultured pollen environment. Thus, the devices can be used for selection of most productive pollen inbred lines in breeding and evaluation of pedigrees for their adaptation to the collection process, with pollen viability and volume pollen collected analyzed individually, by pedigree, enabling large scale pollen selection trials for advancements in commercial scale. The devices also enable time lapse studies to map different physiological shedding windows for pollen and the most productive timing for pollen production by every pedigree sampled.

In one embodiment, an image capture device 138''' may be provided on the pollen collection devices of the present disclosure to image the tassels of the plants to provide a snapshot of the pollen and allow a measurement of the tassels for subsequent analysis such as for all tassel characteristics including those impacting final pollen quantities that can impact tassel risks management, such as blasting, skeletonization, pollen volume, insect damage, tassel size and their interaction with environmental factors that can reduce pollen productivity and pollen yield. The image capture device 138''' also allows for tassel area index towards estimation of pollen volume content per tassel.

In one embodiment, the pollen collection devices of the present disclosure can be used to collect and analyze insects or pests in the field as well as pollen. Therefore, the devices could be used by entomologist as measurement systems for the efficacy of insect repellants.

Modifications and variations of the disclosed embodiments are possible without departing from the scope of the invention defined in the appended claims.

When introducing elements of the present invention or the embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions, products, and methods without departing from the scope of the invention, it is intended that all matter contained in the above description and shown in the accompanying drawings shall be interpreted as illustrative and not in a limiting sense.

What is claimed is:

1. A pollen collection device for collecting pollen from crop plants grown in rows, the device comprising:
   a housing assembly configured to be mounted on a base for being transported through a row of crop plants, the housing assembly including at least one duct defining a pathway for receiving at least a portion of the plants into the at least one duct and directing the at least a portion of the plants through the at least one duct as the housing assembly is transported through the row of crop plants;
   an agitation assembly attached to the housing assembly and positioned generally below the at least one duct, the agitation assembly configured to agitate the plants received into the at least one duct as the housing assembly is transported through the row of crop plants to displace pollen from the plants; and
   a pollen collection assembly attached to the housing assembly at an outlet of the at least one duct for collecting the pollen displaced from the plants as the housing assembly is transported through the row of crop plants, wherein the pollen collection assembly includes:
      a diverter coupled to the pollen collection assembly for diverting the pollen displaced from the plants, the diverter including a housing and an insert received in the housing, and wherein the insert includes a helical vane;
      a receiver coupled to the diverter for receiving the diverted pollen, wherein the insert is selectively positionable within the housing to adjust a distance between the helical vane and the receiver; and
      an air handler configured to produce an airstream flowing through the diverter to the receiver for carrying the displaced pollen to the receiver, wherein the helical vane of the diverter is configured to impart rotation to the airstream to direct the pollen in the airstream radially outward within the diverter.

2. The pollen collection device as set forth in claim 1, wherein the diverter is coupled to tubing of the pollen collection assembly for diverting the pollen displaced from the plants.

3. The pollen collection device as set forth in claim 2, wherein the receiver includes a collection box for receiving the pollen from the diverter and a pollen receptacle removably attached to the collection box.

4. The pollen collection device as set forth in claim 3, wherein the collection box is configured to maintain the collected pollen at a desired temperature and humidity for preserving pollen quality.

5. The pollen collection device as set forth in claim 2, wherein the receiver includes a dead space for receiving the diverted pollen.

6. The pollen collection device as set forth in claim 2, wherein the diverter is arranged generally parallel to the pathway defined by the at least one duct.

7. The pollen collection device as set forth in claim 1, wherein the insert includes a plurality of helical vanes.

8. The pollen collection device as set forth in claim 1, further comprising a continuous system for removing anther or other debris from the pollen.

9. The pollen collection device as set forth in claim 1, further comprising one or more measurement devices for measuring a characteristic of the collected pollen.

10. The pollen collection device as set forth in claim 9, wherein the one or more measurement devices comprise a scale for measuring a weight of the collected pollen, a volume sensor for measuring a volume of the collected pollen, a moisture sensor for detecting a moisture content of the collected pollen, a viability sensor for detecting the ability of the collected pollen to effect fertilization and development, a location sensor for collecting location data to track a location of a plot from which the pollen was collected, and/or a timer for monitoring a time at which the pollen was collected.

11. The pollen collection device as set forth in claim 9, wherein the one or more measurement devices configure the pollen collection device for inbred selection and advancement in a breeding selection process.

12. The pollen collection device as set forth in claim 1, wherein the pathway defined by the at least one duct extends generally horizontally through the at least one duct.

13. A method of collecting pollen from crop plants grown in rows, the method comprising:
transporting a pollen collection device along a row of crop plants, in a direction generally parallel to the row of crop plants;
receiving the crop plants in the row into a pathway defined by a housing assembly of the pollen collection device, the pathway extending in a direction generally parallel to the direction of transport of the pollen collection device;
displacing pollen from the crop plants in the row by contacting an agitator of the pollen collection device with the crop plants as the crop plants are received into the pathway defined by the housing assembly, as the pollen collection device is transported along the row of crop plants;
carrying the displaced pollen to a diverter of a pollen collection assembly of the pollen collection device, wherein the diverter includes a housing and an insert received in the housing;
selectively positioning the insert of the diverter within the housing of the diverter to adjust a distance between a helical vane of the insert and the receiver;
dispersing the pollen displaced from the plants with the diverter; and
collecting the dispersed pollen from the row of crop plants in a receiver of the pollen collection assembly as the pollen collection device is transported along the row of crop plants.

14. The method as set forth in claim 13, further comprising producing an airstream flowing through the diverter to the receiver for carrying the displaced pollen to the receiver.

15. The method as set forth in claim 14, further comprising imparting rotation to the airstream to direct the pollen in the airstream radially outward within the diverter.

16. The method as set forth in claim 13, wherein the receiver includes a collection box for receiving the pollen from the diverter and a pollen receptacle removably attached to the collection box.

17. The method as set forth in claim 13, further comprising receiving the diverted pollen in a dead space in the receiver.

18. The method as set forth in claim 13, further comprising measuring a characteristic of the collected pollen.

19. The method as set forth in claim 18, wherein measuring the characteristic of the collected pollen includes one or more of measuring a weight of the collected pollen, measuring a volume of the collected pollen, and/or measuring a moisture content of the collected pollen.

\* \* \* \* \*